US010190966B2

(12) United States Patent
Matsuda et al.

(10) Patent No.: US 10,190,966 B2
(45) Date of Patent: Jan. 29, 2019

(54) METAL-PIPE USE SUPPORT SYSTEM

(71) Applicant: NIPPON STEEL & SUMITOMO METAL CORPORATION, Tokyo (JP)

(72) Inventors: Yuya Matsuda, Dusseldorf (DE); Takanori Tanaka, Wakayama (JP); Masami Ikeda, Wakayama (JP); Junpei Yashina, Wakayama (JP)

(73) Assignee: NIPPON STEEL & SUMITOMO METAL CORPORATION, Tokyo (JP)

( * ) Notice: Subject to any disclaimer, the term of this patent is extended or adjusted under 35 U.S.C. 154(b) by 0 days.

(21) Appl. No.: 15/320,005

(22) PCT Filed: Jun. 17, 2015

(86) PCT No.: PCT/JP2015/067484
§ 371 (c)(1),
(2) Date: Dec. 19, 2016

(87) PCT Pub. No.: WO2016/002520
PCT Pub. Date: Jan. 7, 2016

(65) Prior Publication Data
US 2017/0138838 A1 May 18, 2017

(30) Foreign Application Priority Data
Jul. 4, 2014 (JP) ................. 2014-139073

(51) Int. Cl.
G01N 17/00 (2006.01)
G06Q 50/04 (2012.01)
(Continued)

(52) U.S. Cl.
CPC .......... *G01N 17/006* (2013.01); *G01B 21/02* (2013.01); *G01L 5/24* (2013.01); *G05B 19/4185* (2013.01);
(Continued)

(58) Field of Classification Search
CPC .................................................. G01N 14/006
See application file for complete search history.

(56) References Cited

U.S. PATENT DOCUMENTS 4,935,195 A * 6/1990 Palusamy .............. G01N 17/00
376/249
2007/0124220 A1 5/2007 Griggs et al.

FOREIGN PATENT DOCUMENTS

JP 2003-084822 3/2003
JP 2008-250714 10/2008
(Continued)

Primary Examiner — Manuel R Rivera Vargas
(74) Attorney, Agent, or Firm — Clark & Brody

(57) ABSTRACT

A metal-pipe use support system (10a) includes: a metal pipe information reception unit (11a) for receiving identification data for each of a plurality of metal pipes; a use condition reception unit (12a) for receiving use condition data about a condition under which a metal pipe is to be used; a pipe-specific data acquisition unit (13a) for accessing a data recording unit (2) storing pipe-specific data indicative of a property of each metal pipe and corresponding identification data in an associated manner and acquiring the pipe-specific data associated with the received identification data; a pipe determination unit (14a) for determining a metal pipe to be used from among the plurality of metal pipes based on the pipe-specific data and the use condition data; and an output unit (15a) for outputting information relating to the determined metal pipe.

13 Claims, 15 Drawing Sheets

(51) Int. Cl.
*G01B 21/02* (2006.01)
*G01L 5/24* (2006.01)
*G05B 19/418* (2006.01)
*G06K 19/06* (2006.01)
*G06Q 10/08* (2012.01)

(52) U.S. Cl.
CPC ..... *G06K 19/06037* (2013.01); *G06Q 10/087* (2013.01); *G06Q 50/04* (2013.01)

(56) References Cited

FOREIGN PATENT DOCUMENTS

| | | |
|---|---|---|
| JP | 2010-139394 | 6/2010 |
| WO | 2008/015871 | 2/2008 |

* cited by examiner

| | | | | |
|---|---|---|---|---|
| PIPE ID | ① | W. No. (Order ID) | WYYK1111 | BYYF2222 |
| | ② | Heat No. (Casting ID) | J1LA111 | J2LB222 |
| | ③ | Pipe No. (Individual pipe ID) | 1111 | 2222 |
| PIPE SPECIFICATION DATA | ④ | Standard for material | SM-125S | L80-130R |
| | ⑤ | Pipe end treatment (e.g. thread type) | VA21 | VATOP |
| | ⑥ | Specified pipe outer diameter (inch) | 13-3/8 | 5-1/2 |
| | ⑦ | Specified individual pipe weight (lb/ft) | 72.0# | 17.0# |
| | ⑧ | Specified pipe length classification | R-3 | R-3 |
| PIPE-SPECIFIC DATA | ⑨ | Measured component value (wt%) | Individual value | Individual value |
| | ⑩ | Measured pipe outer diameter (mm) | 339.85 | 139.98 |
| | ⑪ | Measured pipe wall thickness (mm) | 13.11 | 7.84 |
| | ⑫ | Measured pipe length (mm) | 12861 | 12668 |
| | ⑬ | Measured pipe ellipticity (%) | 0.21 | 0.24 |
| | ⑭ | Maximum defect depth (mm) | 0.2 | 0.1 |
| | ⑮ | YS tensile strength (ksi) | 126.2 | 85.6 |
| | ⑯ | HRC hardness | 31.2 | 20.9 |
| | ⑰ | Impact value (J) | 95 | 88 |
| | ⑱ | Thread-fastening torque value (N·m) | 59355 | 7521 |
| | ⑲ | Calculated collapse value (psi) | 7314 | 5876 |
| | ⑳ | Calculated value of coefficient of corrosion resistance | 3.75 | 1.31 |

METAL-PIPE USE SUPPORT SYSTEM

TECHNICAL FIELD

The present invention relates to a technique for processing data relating to metal pipes using a computer and supporting the use of metal pipes.

BACKGROUND ART

Methods have been proposed for managing quality information where quality information provided during manufacture of steel products is shared by the manufacturer and customer. For example, JP 2003-84822 A describes a management method whereby quality information provided during manufacture of steel products is stored in a database by the manufacturer of these steel products and the stored quality information can be read online by a customer.

Further, kinds of quality information about steel pipes managed on a database have been proposed. For example, JP 2010-139394 A discloses an analysis method for providing at least one of the following kinds of information about a manufactured steel product: information about the composition of precipitates or the like; information about the sizes of precipitates or the like; and information about the solid solution amount of the element in interest. The analyzed information about precipitates and solid solution is stored as a management database.

A technique for identifying a steel pipe during the manufacturing process is described in, for example, WO 2008/015871 A, where the pipe is processed such that an identifier is formed at a position to be subjected to thread cutting. JP 2008-250714 A describes mounting an RFID tag on the pipe body of a seamless steel pipe or on a pipe end protector.

DISCLOSURE OF THE INVENTION

The above conventional techniques make product information about each metal pipe available to the user of the metal pipe. However, there is no mechanism for providing information that would serve as a guide about how to select produced metal pipes with slightly different properties and how to arrange them under specific use conditions. For example, in an oil well, a plurality of metal pipes that meet predetermined specifications are used, where the metal pipes that meet the specifications may have slightly different properties, such as different sizes or different pressure resistances. If this is the case, even if information about properties of each metal pipe is available, it is difficult for someone at the site of work to decide on an appropriate arrangement of the metal pipes taking into consideration the environment in the oil well pit and properties of each metal pipe.

In view of this, present application discloses a computer system that provides information useful in appropriately using metal pipes having properties suitable for the conditions under which the metal pipes are to be used.

A metal-pipe use support system according to an embodiment of the present invention includes: a metal pipe information reception unit configured to receive identification data for each of a plurality of metal pipes; a use condition reception unit configured to receive use condition data about a condition under which a metal pipe is to be used; a pipe-specific data acquisition unit configured to access a data recording unit storing pipe-specific data indicative of a property of each metal pipe and corresponding identification data in an associated manner and to acquire the pipe-specific data associated with the identification data received by the metal pipe information reception unit; a pipe determination unit configured to determine a metal pipe to be used from among the plurality of metal pipes based on the pipe-specific data acquired by the pipe-specific data acquisition unit and the use condition data; and an output unit configured to output information relating to the metal pipe determined by the pipe determination unit.

The disclosure of the present application realizes a computer system that provides information useful in appropriately using metal pipes having properties suitable for the conditions under which the metal pipes are to be used.

BRIEF DESCRIPTION OF THE DRAWINGS

FIG. 6 shows an example table containing pipe-specific data.

EMBODIMENTS FOR CARRYING OUT THE INVENTION

Figure 1:
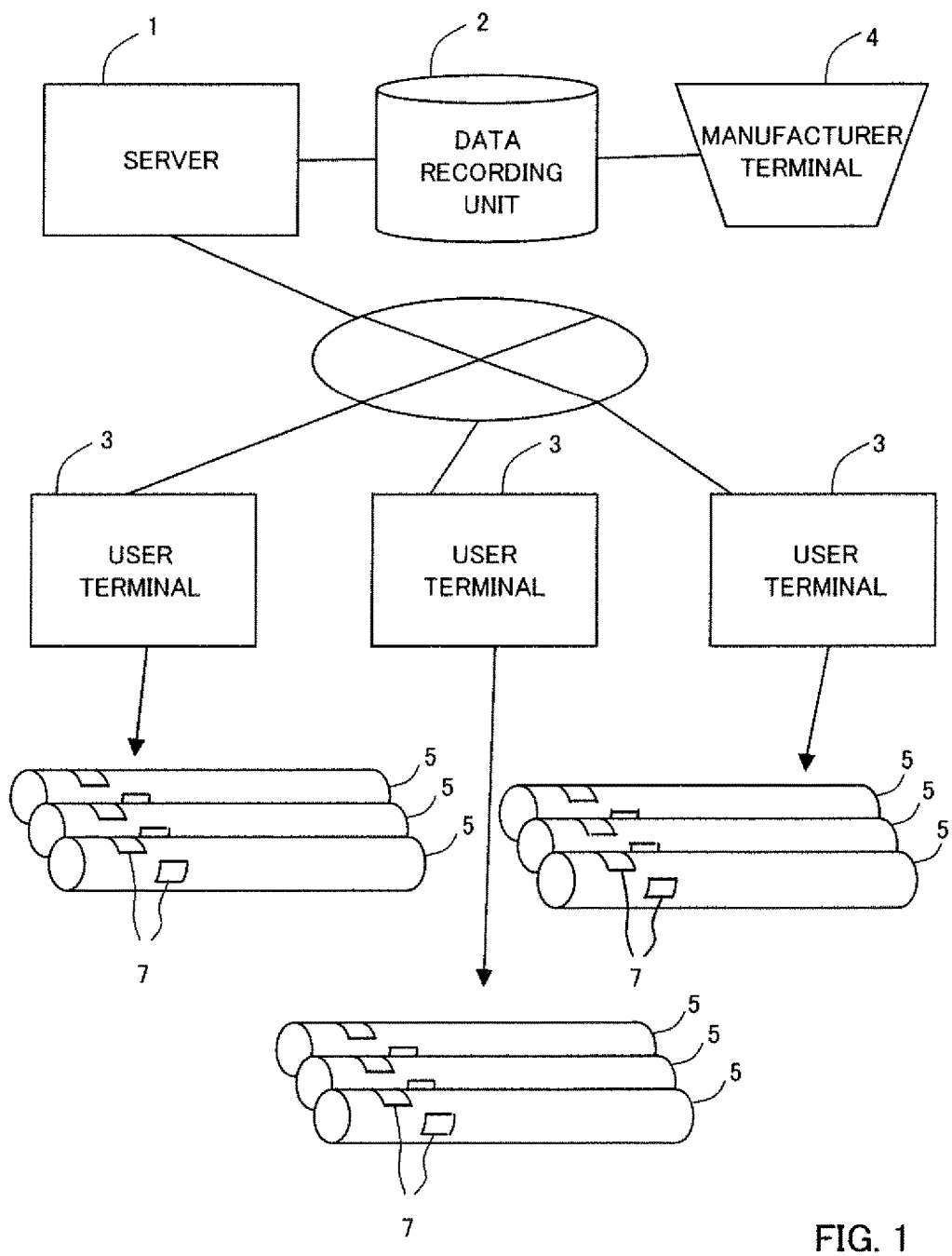
FIG. 1 illustrates a configuration of a system including a metal-pipe use support system according to the present embodiment.

A metal-pipe use support system according to an embodiment of the present invention includes: a metal pipe information reception unit configured to receive identification data for each of a plurality of metal pipes; a use condition reception unit configured to receive use condition data about a condition under which a metal pipe is to be used; a pipe-specific data acquisition unit configured to access a data recording unit storing pipe-specific data indicative of a property of each metal pipe and corresponding identification data in an associated manner and to acquire the pipe-specific data associated with the identification data received by the metal pipe information reception unit; a pipe determination unit configured to determine a metal pipe to be used from among the plurality of metal pipes based on the pipe-specific data acquired by the pipe-specific data acquisition unit and the use condition data; and an output unit configured to output information relating to the metal pipe determined by the pipe determination unit.

In the above arrangement, the metal pipe information reception unit and pipe-specific data acquisition unit provide pipe-specific data indicating the properties of each of a plurality of metal pipes. The pipe determination unit determines the metal pipe to be used from among the plurality of metal pipes based on this pipe-specific data and use condition data relating to the conditions under which metal pipes are to be used. This enables determining the metal pipe with properties suitable for the conditions under which metal pipes are to be used to be the metal pipe to be used. The output unit outputs information about the determined metal pipe. This provides information useful in appropriately using a metal pipe depending on the conditions and the properties of metal pipes.

The pipe determination unit may decide on a connection relationship between a plurality of metal pipes determined to be metal pipes to be used. This provides information that enables appropriately connecting a plurality of metal pipes depending on the use conditions of metal pipes. For example, information may be provided that enables appropriate arrangement of a plurality of metal pipes suitable for the environment in which metal pipes are to be placed.

The pipe-specific data acquired by the pipe-specific data acquisition unit may include a measured value of the property of each of the plurality of metal pipes or a value calculated from the measured value. Using pipe-specific data that is based on a measured value enables determining the metal pipe suitable for use conditions taking the actual properties of the metal pipes into consideration.

The use condition data may include data indicative of an underground environment in which a metal pipe is to be placed, and the pipe-specific data acquired by the pipe-specific data acquisition unit may include data indicative of a pressure resistance of each of the plurality of metal pipes. In this case, based on the underground environment indicated by the use condition data and the pressure resistance of each of the plurality of metal pipes indicated by the pipe-specific data, the pipe determination unit may decide to place a metal pipe that has a pressure resistance suitable for the underground environment to decide on a connection relationship between at least two of the plurality of metal pipes. This provides information that can be used to appropriately place metal pipes having a pressure resistance suitable for an underground environment in which metal pipes are to be placed.

The use condition data may include data indicative of an underground environment in which a metal pipe is to be placed, and the pipe-specific data may include data indicative of a corrosion resistance of each of the plurality of metal pipes. In this case, based on the underground environment indicated by the use condition data and the corrosion resistance of each of the plurality of metal pipes indicated by the pipe-specific data, the pipe determination unit may decide to place a metal pipe having a corrosion resistance suitable for the underground environment to decide on a connection relationship between at least two of the plurality of metal pipes. This provides information that can be used to appropriately place metal pipes having a corrosion resistance suitable for the underground environment in which metal pipes are to be placed.

The pipe-specific data acquired by the pipe-specific data acquisition unit may include data indicative of a size and shape of each of the plurality of metal pipes. In this case, based on the size and shape indicated by the pipe-specific data, the pipe determination unit may decide on a connection relationship between at least two of the plurality of metal pipes. This provides information that can be used to connect metal pipes with mutually conforming sizes and shapes.

The use condition data may include data indicative of a performance required of a processed good made from a metal pipe. In this case, the pipe determination unit may determine, from among the plurality of metal pipes, at least one metal pipe that has a property meeting the performance required of the processed good indicated by the use condition data. This provides information that can be used to select a metal pipe suitable to be a processed product.

The use condition data may include an upper limit of a length of a metal pipe, and the pipe-specific data acquired by the pipe-specific data acquisition unit may include a measured length of each of the plurality of metal pipes. The pipe determination unit may determine, from among the plurality of metal pipes, at least one metal pipe having a measured length not exceeding the upper limit. This provides information about metal pipes each having a length that actually does not exceed an upper limit.

The use condition data may include data indicative of a degree of risk that a threaded joint for metal pipes tightened during a manufacture process loosens in an environment in which the metal pipes are placed, and the pipe-specific data acquired by the pipe-specific data acquisition unit may include data indicative of a tightening torque for a threaded joint for the plurality of metal pipes. In this case, the pipe determination unit decide to place a metal pipe having a tightening torque suitable for the degree of risk indicated by the use condition data to decide on a connection relationship between at least two of the plurality of metal pipes. This provides information that can be used to place metal pipes each having an appropriate tightening torque depending on the degree of risk of thread loosening under the conditions under which metal pipes are to be placed.

The use condition data may include data indicative of a degree of risk of breaking or corrosion-induced wall thinning of a metal pipe in an environment in which the metal pipe is to be placed, and the pipe-specific data acquired by the pipe-specific data acquisition unit may include data indicative of a flaw on each of the plurality of metal pipes. In this case, the pipe determination unit decides to place a metal pipe having a flaw acceptable under the degree of risk of breaking or corrosion-induced wall thinning indicated by the use condition data to decide on a connection relationship between at least two of the plurality of metal pipes. This provides information that enables appropriate arrangement of metal pipes based on the risk of breaking or corrosion in an environment in which metal pipes are to be placed and on the extent of flaws on metal pipes.

The pipe-specific data may include data indicative a length and weight of each of the plurality of metal pipes. In this case, when a predetermined number of metal pipes are connected to form a set and a plurality of such sets are provided, the pipe determination unit may determine a combination of predetermined number of metal pipes in each set that will result in a near-uniform length and weight of the sets of metal pipes. This provides information that can be used to provide a plurality of sets of connected metal pipes with a uniform set length and set weight.

Also, a method of operating the above-described metal-pipe use support system is included in embodiments of the present invention. Further, a metal pipe use support program for causing a computer to implement the units of the above-described metal-pipe use support system and a non-transitory storage medium storing such a metal pipe use support program are included in embodiments of the present invention.

Now, embodiments of the present invention will be described in detail with reference to the drawings. In the drawings, the same or corresponding components are labeled with the same characters and their description will not be repeated.

Embodiment 1

<System Configuration>

FIG. 1 shows a configuration of a system including a metal-pipe use support system in the present embodiment. In the implementation shown in FIG. 1, a server 1 and user terminals 3 can communicate over a network. The server 1 is capable of accessing a data recording unit 2. The data recording unit 2 is accessible to a manufacturer terminal 4. Each user terminal 3 is capable of reading an identification mark 7 attached to each metal pipe 5. The metal-pipe use support system may be implemented by the server 1 or by each user terminal 3, for example.

The data recording unit 2 stores pipe-specific data indicative of the properties of each metal pipe and identification data in an associated manner. The data recording unit 2 may be implemented by a recording device (i.e. storage) accessible to the server 1, for example. The pipe-specific data may include, for example, a measured size of the metal pipe and measured values of results of various inspections and tests, as well as values derived from measured values. Values derived from measured values may be, for example, values indicative of the performance of the metal pipe calculated from measured values. For example, the pipe-specific data may be stored in the data recording unit 2 in the format of a relational database table. The pipe-specific data is not limited to a particular data format. The pipe-specific data may be supplied via the manufacturer terminal 4, for example.

<Metal-Pipe Use Support System Implemented in Server>

Figure 2:
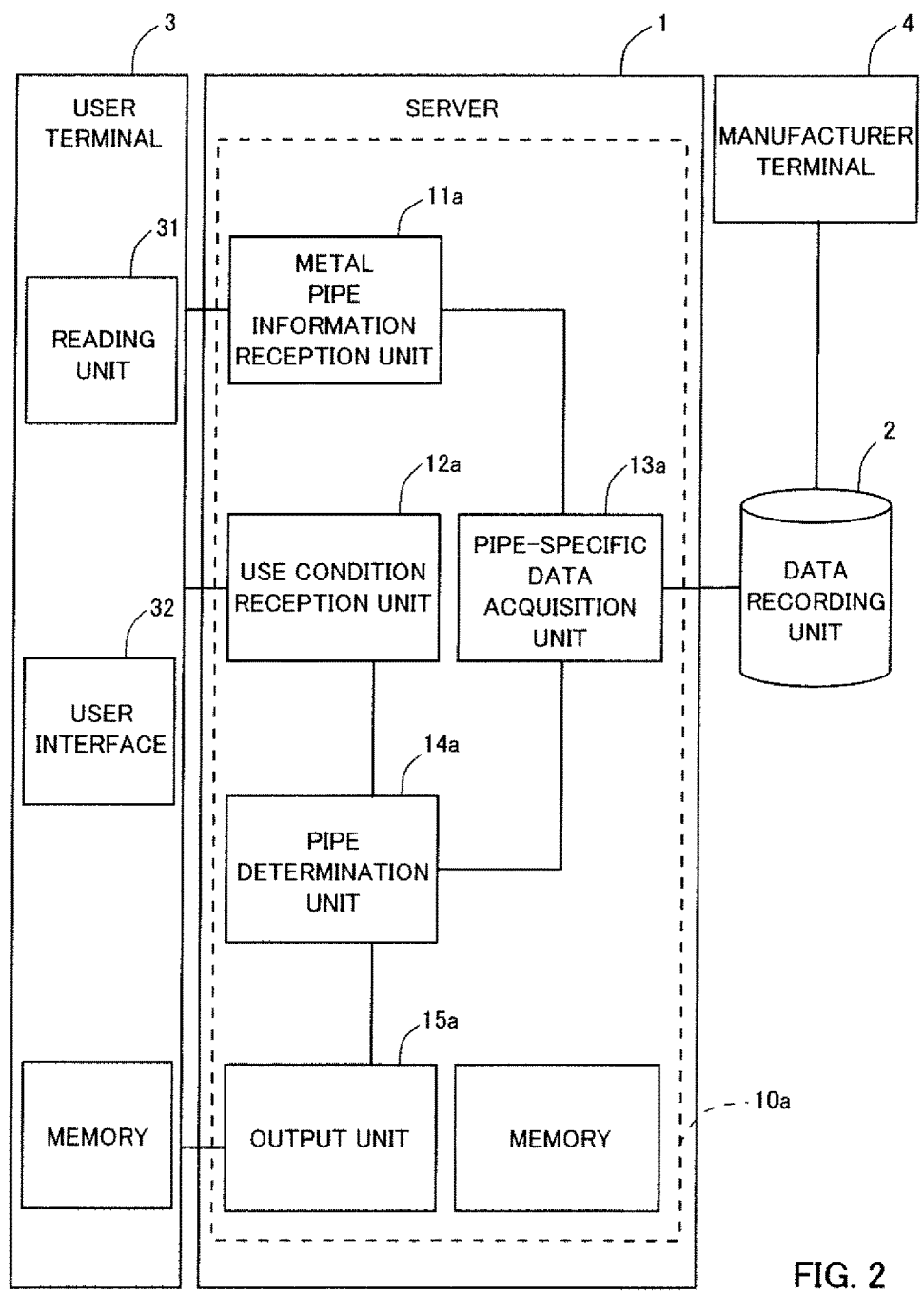
FIG. 2 is a block diagram of a configuration in which a metal-pipe use support system 10a is built in the server 1 shown in FIG. 1.

FIG. 2 is a block diagram of a configuration of a metal-pipe use support system 10a built in the server 1. In the implementation shown in FIG. 2, the metal-pipe use support system 10a built in the server 1 includes a metal pipe information reception unit 11a, a use condition reception unit 12a, a pipe-specific data acquisition unit 13a, a pipe determination unit 14a, and an output unit 15a. A user terminal 3 includes a reading unit 31 for reading an identification mark on a metal pipe 5 and a user interface 32 for providing a display for a user and receiving input from the user.

The metal pipe information reception unit 11a receives identification data for each of a plurality of metal pipes read by the user terminal 3. For example, the metal pipe information reception unit 11a stores, in a memory in the server 1, identification data for each of the metal pipes transmitted from the user terminal 3 such that the data is accessible to the pipe-specific data acquisition unit 13a and pipe determination unit 14a. The pipe-specific data acquisition unit 13a accesses the data recording unit 2 to acquire pipe-specific data associated with the identification data received by the metal pipe information reception unit 11a.

The metal specific data acquisition unit 13a reads, from the data recording unit 2, the stored pipe-specific data stored so as to be associated with the identification data received by the metal pipe information reception unit 11a to acquire the pipe-specific data.

The use condition reception unit 12a receives, from the user terminal 3, use condition data relating to the conditions under which metal pipes are to be used. The use condition reception unit 12a may store the use condition data transmitted by the user terminal 3 in the memory in the server 1. The use condition data may be, for example, data indicating under which conditions metal pipes are to be used or in what environment metal pipes are to be used. The use condition data is entered by the user via the user terminal 3.

Based on the pipe-specific data acquired by the pipe-specific data acquisition unit 13a and on the use condition data received by the use condition reception unit 12a, the pipe determination unit 14a determines the metal pipes to be used from among the plurality of metal pipes indicated by the identification data received by the metal pipe information reception unit 11a. Further, the pipe determination unit 14a may decides on a connection relationship between the metal pipes determined to be the metal pipes to be used. For example, the pipe determination unit 14a may compare the use condition data with the pipe-specific data of the metal pipes to determine the metal pipes having properties suitable for the conditions indicated by the use condition data or decide on a connection order of the metal pipes. For example, the pipe determination unit 14a may determine the appropriate metal pipes or the appropriate connection order of metal pipes based on a comparison between conditions provided by the use condition data and the properties of each of the metal pipes indicated by the pipe-specific data or the properties of a group of connected metal pipes.

The output unit 15a transmits information about the metal pipes determined by the pipe determination unit 14a to the user terminal 3. The output unit 15a may transmit, for example, the identification data for the metal pipes determined by the pipe determination unit 14a or data indicative of the connection order of the metal pipes to the user terminal 3.

<Operation>

Figure 3:
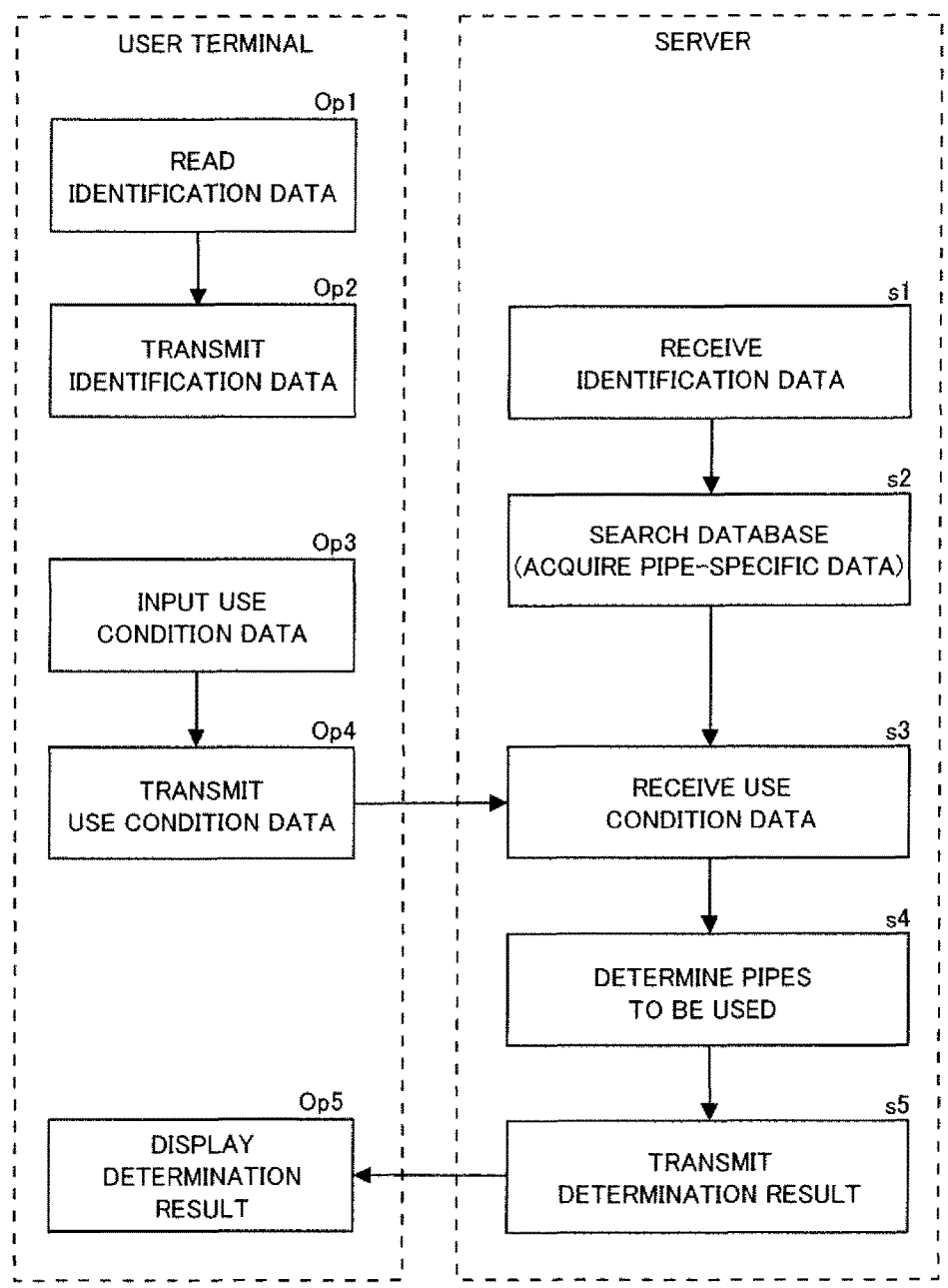
FIG. 3 is a flow chart illustrating an operation of the metal-pipe use support system 10a shown in FIG. 2.

FIG. 3 is a flow chart illustrating an operation of the metal-pipe use support system 10a shown in FIG. 2. In the implementation shown in FIG. 3, identification data for a metal pipe is read by the user terminal 3 as an identification mark 7 such as two-dimensional code (2D code), for example, on the metal pipe 5 is read by the reading unit 31 of the user terminal 3 (Op1). The user terminal 3 transmits the identification data to the server 1 (Op2). The metal pipe information reception unit 11a of the server 1 receives the identification data from the user terminal 3 (s1). The metal pipe information reception unit 11a may instruct the user terminal 3 to read the identification data for a plurality of metal pipes and transmit identification data to the server 1. Alternatively, the user terminal 3 may transmit to the server 1 a query about metal pipes to be used together with the identification data for a plurality of metal pipes and use condition data without waiting for an instruction from the metal-pipe use support system 10a.

The pipe-specific data acquisition unit 13a uses the identification data received at s1 as a search key to search the database in the data recording unit 2 (s2). The pipe-specific data acquisition unit 13a acquires search results, i.e. pipe-specific data associated with the identification data received at s1.

The user enters use condition data or data to be used to provide use condition data into the user terminal 3 via the user interface 32 (Op3). The use condition data entered may be, for example, application conditions for metal pipes, such as the conditions of wells into which metal pipes are to be deployed. The user terminal 3 transmits the use condition data to the server 1 (Op4). The use condition reception unit 12a receives the use condition data from the user terminal 3 (s3). The reception of the use condition data at s3 may occur before s2 or s1. The use condition reception unit 12a may request use condition data from the user terminal 3. For example, the use condition reception unit 12a may transmit, to the user terminal 3, data that can be used to provide a screen into which the user can enter use condition data, thereby prompting the user terminal 3 to display this screen.

As an example, an implementation will be described where the use condition data received at s3 is data relating to the environment in which metal pipes are to be placed. Data relating to the environment in which metal pipes are to be placed may be, for example, the pressure at the location where each metal pipe is to be placed, the depth underground, geological features, or the amount of a particular component in gasses that will pass through the pipe, the degree of risk of thread loosening, or the degree of risk of a break.

Based on the pipe-specific data received at s2 and the use condition data received at s3, the pipe determination unit 14a determines the metal pipe to be used from among the plurality of metal pipes indicated by the identification data received at s1 (s4). For example, if the use condition data received is data indicating the distribution of an environment value (for example, pressure) indicative of the environment of the space in which metal pipes are to be placed, the pipe determination unit 14a can decide on an arrangement of metal pipes based on performance values (for example, pressure resistance) indicative of the performance of the metal pipes indicated by the pipe-specific data and on the environment value indicated by the use condition data.

For example, the pipe determination unit 14a may assign, to each of the positions in the space in which metal pipes are to be placed, a metal pipe having a performance value suitable for the environment value of that position to decide on an arrangement. More specifically, the pipe determination unit 14a may sort a plurality of metal pipes based on a performance value in the pipe-specific data and consecutively assign the sorted metal pipes to positions in the arrangement depending on the environment value. Alternatively, the pipe determination unit 14a may determine the connection order of metal pipes that minimizes the degree of unconformity of the performance value of each of the arranged metal pipes relative to the associated environment value.

The output unit 15a transmits to the user terminal 3 the metal pipes to be used determined at s4 or the connection order of the metal pipes to be used (s5). The output unit 15a may prompt the user terminal 3 to display information relating to the metal pipes to be used determined at s4 (Op5).

<Metal-Pipe Use Support System Implemented in User Terminal>

Figure 4:
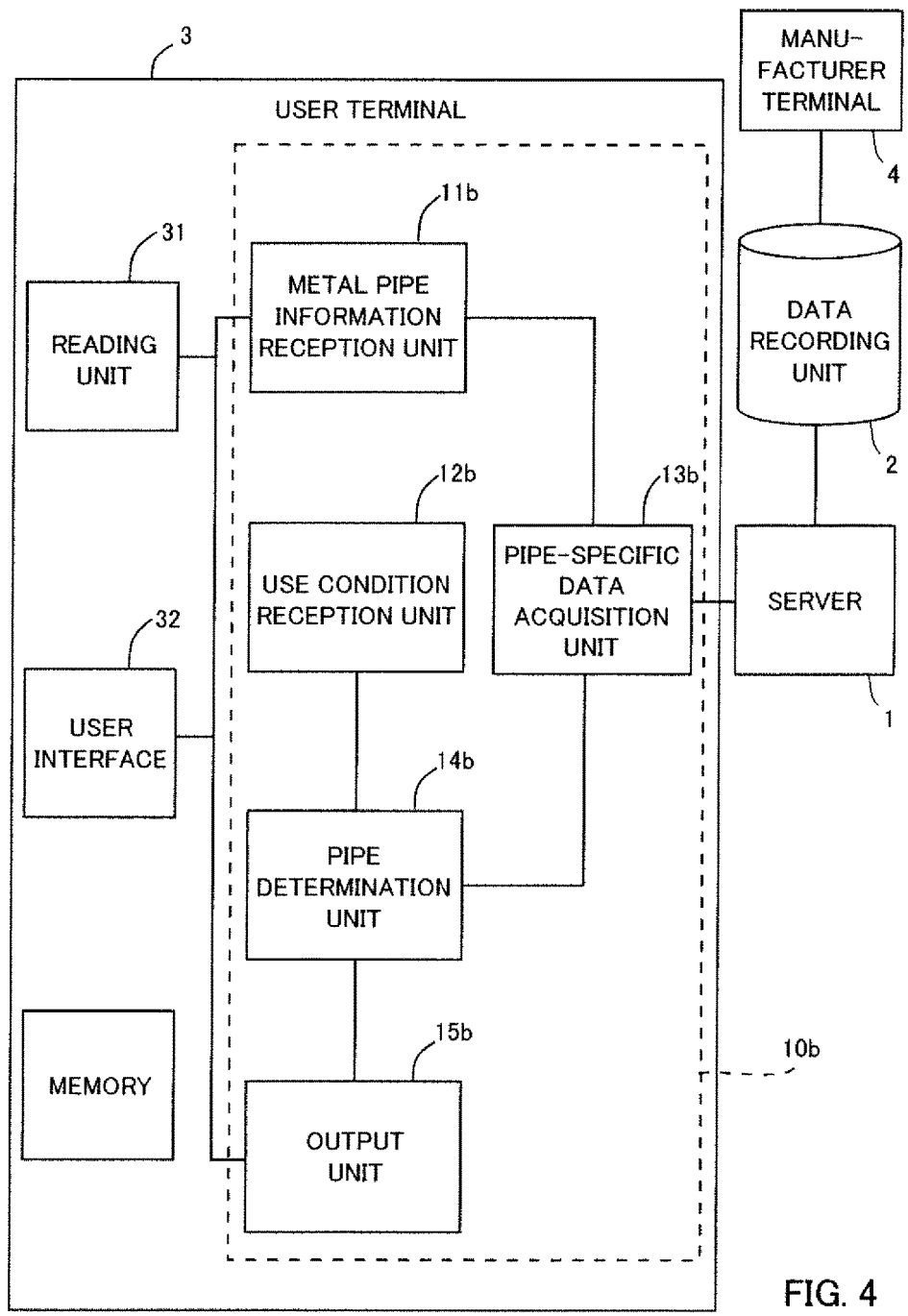
FIG. 4 is a block diagram of a configuration in which a metal-pipe use support system 10b is implemented by the user terminal 3 shown in FIG. 1.

FIG. 4 is a block diagram of a configuration of a metal-pipe use support system 10b implemented by a user terminal 3. In the implementation shown in FIG. 4, the metal-pipe use support system 10b built in the user terminal 3 includes a metal pipe information reception unit 11b, a use condition reception unit 12b, a pipe-specific data acquisition unit 13b, a pipe determination unit 14b, and an output unit 15b. The user terminal 3 includes a reading unit 31 for reading an identification mark 7 on a metal pipe 5 and a user interface 32 for providing a display for a user and receiving input from the user (hereinafter referred to as UI unit 32).

The metal pipe information reception unit 11b works together with the UI unit 32 and reading unit 31 to acquire identification data for each of a plurality of metal pipes read by the reading unit 31. For example, the metal pipe information reception unit 11b may use the UI unit 32 to prompt the user to conduct operations for reading the identification mark 7 on each metal pipe 5. Further, the metal pipe information reception unit 11b controls the reading unit 31 based on read instructions by the user entered via the UI unit 32 to read the identification mark 7 on each of the metal pipes 5. The identification data read by the reading unit 31 is stored in a memory in the user terminal 3 such that it is accessible to the pipe-specific data acquisition unit 13b and pipe determination unit 14b.

The pipe-specific data acquisition unit 13b accesses a data recording unit 2 via a server 1 to acquire the pipe-specific data associated with identification data received by the metal pipe information reception unit 11b. The pipe-specific data acquisition unit 13b may transmit a request for the pipe-specific data and identification data to the server 1. Upon reception of the request from the pipe-specific data acquisition unit 13b, the server 1 acquires the pipe-specific data associated with the transmitted identification data from the data recording unit 2. The pipe-specific data acquisition unit 13b may receive from the server 1 the pipe-specific data acquired from the data recording unit 2, and store it in the memory. Alternatively, the pipe-specific data acquisition unit 13b may ensure that the pipe-specific data retrieved from the server 1 can be referred to by the pipe-specific data acquisition unit 13b or pipe determination unit 14b. In such implementations, the pipe-specific data need not be stored in the memory in the user terminal 3.

The use condition reception unit 12b receives from the user, via the UI unit 32, input of use condition data relating to conditions under which metal pipes are to be used. For example, the use condition reception unit 12b may prompt the UI unit 32 to display a screen into which the user can enter information that will be used to provide use condition data.

Based on the pipe-specific data acquired by the pipe-specific data acquisition unit 13b and the use condition data received by the use condition reception unit 12b, the pipe determination unit 14b determines the metal pipes to be used from among the plurality of metal pipes indicated by the identification data received by the metal pipe information reception unit 11b. The pipe determination unit 14b may have the same configuration as that of the pipe determination unit 14a.

The output unit 15b outputs information relating to the metal pipes determined by the pipe determination unit 14b via the UT unit 32 for the user. For example, the output unit 15b may display information about the metal pipes to be used on a display (not shown) included in the user terminal 3.

<Operation>

Figure 5:
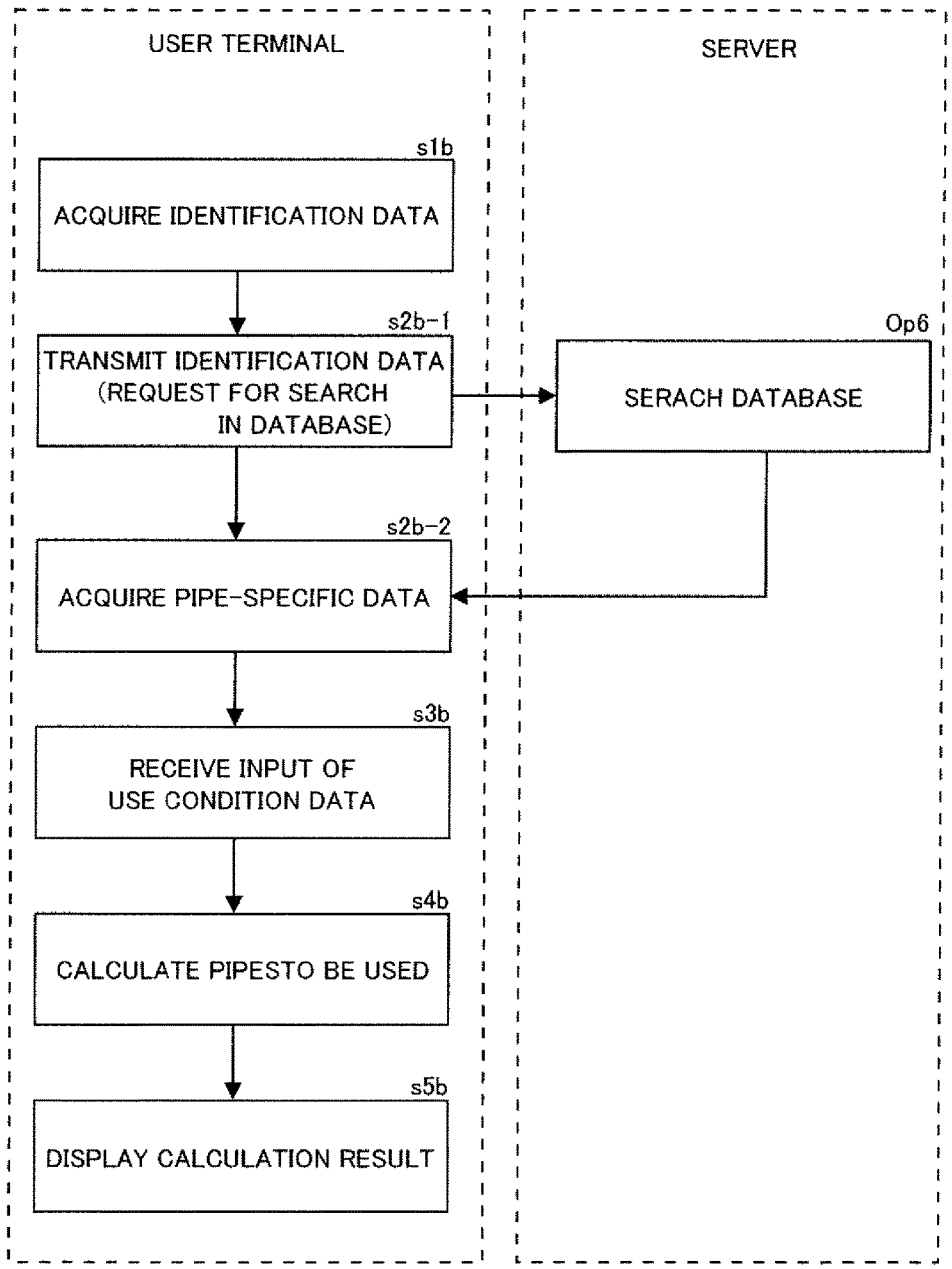
FIG. 5 is a flow chart illustrating an operation of the metal-pipe use support system 10b shown in FIG. 4.

FIG. 5 is a flow chart indicating an operation of the metal-pipe use support system 10b shown in FIG. 4. In the implementation shown in FIG. 5, the metal pipe information reception unit 11b acquires identification data of a plurality of metal pipes read by the reading unit 31 of the user terminal 3 (s1b). The metal pipe information reception unit 11b controls the reading unit 31 and UI unit 32 to support the user in operations for reading the identification mark on each metal pipe.

The pipe-specific data acquisition unit 13b transmits the identification data acquired at s1b to the server 1 to request the server to search for pipe-specific data (s2b-1). The server 1 searches a database in the data recording unit 2 storing identification data and pipe-specific data in an associated manner (Op6). The pipe-specific data acquiring unit 13b receives from the server 1 search results, i.e. the pipe-specific data associated with the identification data received at s1*b* (s2*b*-2). In this way, the pipe-specific data acquisition unit 13*b* may access the data recording unit 2 via the server 1. Alternatively, the pipe-specific data acquisition unit 13*b* may receive, instead of pipe-specific data, data that allows the unit to access pipe-specific data.

The use condition reception unit 12*b* receives input of the use condition data from the user (s3*b*). The reception of the use condition data at s3*b* may occur before s2*b*-1, s2*b*-2 or s1*b*. For example, the use condition reception unit 12*b* may prompt the UI unit 32 to display a screen into which the user can enter use condition data.

The use condition data acquired at s3*b* may be, for example, data relating to an environment in which metal pipes are to be placed, as is the case with s3 in FIG. 3. Another implementation will be described where the use condition data entered at s36 is data indicating a condition under which metal pipes are to be used. Data indicating a condition under which metal pipes are to be used may be, for example, the number of metal pipes to be used, the number of metal pipes to be connected, the upper limit of length of metal pipes, the performance value required if metal pipes are to be processed, or the number of metal pipes connected to form a set for use.

Based on the pipe-specific data received at s2*b*-2 and the use condition data received at s3*b*, the pipe determination unit 14*b* determines the metal pipe to be used from among the plurality of metal pipes indicated by the identification data received at s1*b* (s4*b*). For example, if the use condition data received is data indicating a condition under which metal pipes are to be used (for example, the number of metal pipes to be used), the pipe determination unit 14*b* may determine the metal pipe or the connection order of metal pipes that meets the use condition or the metal pipe or the connection order of metal pipes that meets the use condition and has good properties.

The output unit 15*b* displays on the display of the user terminal 3, via the UI unit 32, the metal pipe to be used or the connection order of metal pipes to be used determined at s4*b* (s5*b*).

The configurations shown in FIGS. 2 and 4 and the operations shown in FIGS. 3 and 5 enable presenting, on the user terminal, metal pipes or a connection order thereof that meet the conditions required when the user uses the metal pipes. This allows the user to appropriately use metal pipes having properties suitable for use conditions.

For example, the metal pipes delivered to the user meet predetermined specifications. In connection with a plurality of metal pipes meeting specifications, the measured size values, the results of nondestructive inspections, the measured values of mechanical properties, the component values and other values are often different, though within the specification tolerances. Data indicating such properties specific to individual metal pipes may be used as pipe-specific data. In this case, the user, at the site of using metal pipes, may cause the metal-pipe use support system to process the identification data of the metal pipes read by the user terminal 3 to learn which metal pipes or which connection order thereof is suitable for the use conditions at the site of work and the properties of the metal pipes that are present at the site of work.

The configuration and operation of the metal-pipe use support system are not limited to the above-illustrated implementations. For example, the various units of the metal-pipe use support system 10*b* and the data recording unit 2 may be included in a single user terminal 3. In other words, the metal-pipe use support system may operate as a stand-alone system. Alternatively, the various units of the metal-pipe use support system 10*b* may be distributed among a plurality of computers. For example, the user terminal 3 and server 1 may implement the metal-pipe use support system 10*b*.

The metal pipe information reception units 11*a* and 11*b*, use condition reception units 12*a* and 12*b*, pipe-specific data reception units 13*a* and 13*b*, pipe determination units 14*a* and 14*b* and output units 15*a* and 15 of the metal-pipe use support systems 10*a* and 10*b* may be implemented by the computer of the server 1 or user terminal 3. That is, one or more processors may read a program from a memory such as a ROM or RAM and execute this program to implement the above-illustrated units. An application program installed into the server 1 or user terminal 3 to enable performing the operations of the various units described above is also included in embodiments of the present invention.

<Configuration of Identification Mark on Metal Pipe>

An example of the identification mark 7 on the metal pipe 5 read by the user terminal 3 of the metal-pipe use support system 10*a* or 10*b* will be described. The indication mark 7 on the metal pipe 5 is not limited to a particular format, and may be an RFID tag or two-dimensional code, for example. The two-dimensional code may be formed on the surface of the metal pipe 5 by ink-jet printing, a label seal, printing using a laser, or an impressed seal, for example. Ink-jet printing provides two-dimensional code with high readability (visibility) and does not significantly affect the performance of the metal pipe, and provides good durability. Further, ink-jet printing is more advantageous than other methods in terms of print work environment and print rate. Printing using a laser provides two-dimensional code with good durability.

The identification mark 7 may be positioned at any location; a plurality of identification marks 7 may be positioned at different locations on the outer surface of the metal pipe to eliminate position dependence in reading. For example, a plurality of identification marks may be provided at different locations distributed in the circumferential and axial directions the cylindrical metal pipe.

Example of Data in Data Recording Unit 2

FIG. 6 illustrates an example of a table containing pipe-specific data. In the example shown in FIG. 6, pipe identification data, pipe specification data and pipe-specific data are stored in an associated manner. One row includes pipe the identification data as well as the pipe specification data and pipe-specific data of the pipe identified by this identification data, all of which constitute one data item.

In the example shown in FIG. 6, the pipe ID includes an individual pipe ID that serves as identification data identifying the individual metal pipe, as well as IDs identifying the channel of distribution and manufacturing process of the metal pipe, such as order ID or casting ID. The pipe specification data includes data indicating technical requirements to be met by the metal pipe. The pipe-specific data includes data indicating the properties specific to the individual metal pipe. In the present example, the pipe-specific data indicating properties of the particular pipe that may be different from those of other pipes while remaining within the specification tolerance is treated as separate from the pipe specification data which indicates the specifications of a metal pipe. The pipe-specific data in this example includes measured values of the size and shape of the metal pipe and measured values obtained from various measurements, tests and inspections as well as values derived from these measurement values. For example, the calculated collapse value (19) in FIG. 6 may be calculated from the measured pipe outer diameter (10), measured pipe wall thickness (11), measured pipe ellipticity (13) and YS tensile strength (15). The calculated value of coefficient of corrosion resistance (20) may be calculated from the measured component value (9) and HRC hardness (16). Alternatively, the specification data and the data based on measured values may both be treated as pipe-specific data.

The embodiments illustrated below discuss specific examples of processes by the metal-pipe use support system 10*a* or 10*b* for using the pipe-specific data shown in FIG. 6 to determine the metal pipes to be used or the order thereof. In the following description, when the metal-pipe use support system 10*a* and metal-pipe use support system 10*b* are not distinguished, they will be simply referred to as metal-pipe use support system 10 without the letters a and b. Similarly, the letters a and b will be omitted from the reference numerals for the units in the metal-pipe use support system 10.

Embodiment 2

<Process of Determining Arrangement of Metal Pipes with Pressure Performance Suitable for Underground Environment>

Figure 7:
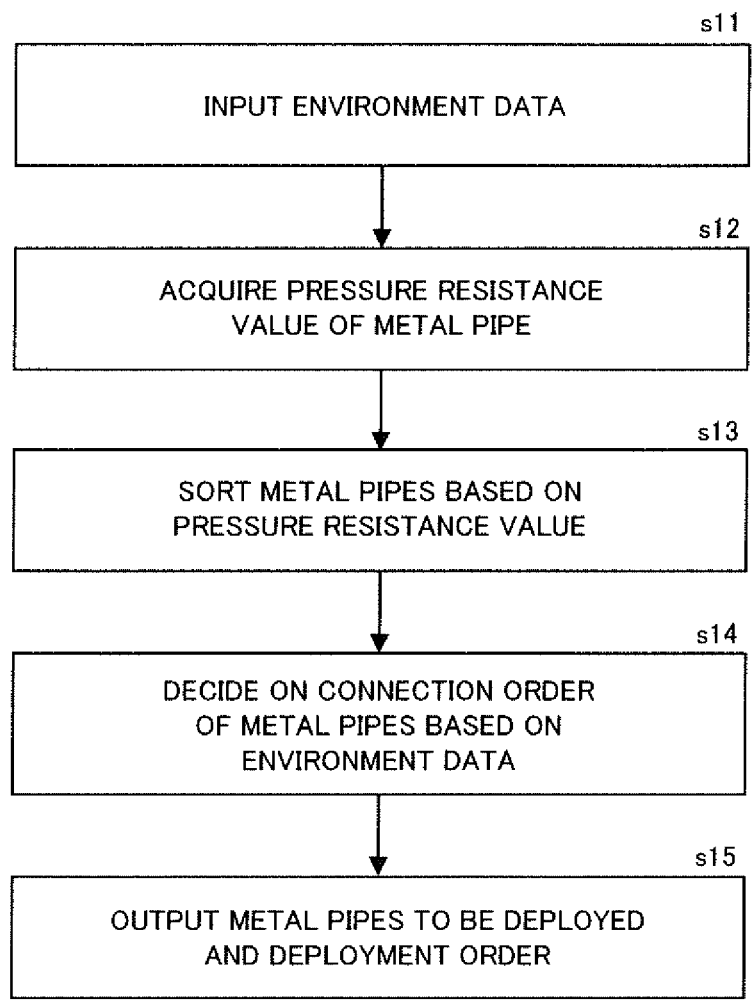
FIG. 7 is a flow chart illustrating a process for deciding on a connection order of metal pipes.

FIG. 7 is a flow chart illustrating an example of a process for deciding on a connection order of metal pipes. In the example shown in FIG. 7, the use condition reception unit 12 acquires, as the use condition data, environment data indicating the environment in which metal pipes are to be placed (s11). The environment data acquired may be data indicating, for example, the depth of the oil well in which metal pipes are to be placed, oil-well pit angle, pressure distribution, the relationship between pressure and depth, and geological features.

The pipe-specific data acquisition unit 13 acquires, as the pipe-specific data, pressure resistance data indicating the pressure resistance of each of a plurality of metal pipes (s12). The pressure resistance data acquired may be, for example, the collapse strength which indicates the crush resistance against an external pressure, tensile strength, or HRC hardness.

The pipe determination unit 14 rearranges (or sorts) the metal pipes indicated by the identification data acquired by the metal pipe information reception unit 11 based on their pressure resistance values (s13). Based on the order of the rearranged metal pipes and the environment data, the pipe determination unit 14 determines the metal pipes to be used and the connection order of these metal pipes (s14).

For example, based on the environment data acquired as the use condition data, the pipe determination unit 14 determines the pressure at the underground position at which the metal pipe is to be placed or the degree of pressure resistance required of the metal pipe. Then, the pipe determination unit 14 may determine the connection order of the metal pipes that ensures that a metal pipe with a pressure resistance higher than other metal pipes is positioned at an underground position at which the pressure or the pressure resistance required is higher than those at other positions. More specifically, the pipe determination unit 14 may divide the space in which the metal pipes are to be placed into a plurality of sections with different pressures or required pressure resistances and assign metal pipes sorted at s13 to sections with higher pressures or required pressure resistances and then sections with lower pressures or required pressure resistances in descending order.

Alternatively, the pipe determination unit 14 may compare the pressure resistances of metal pipes connected together and placed underground and the pressures or required pressure resistances at these positions and, based on the result of this comparison, perform a process of evaluating the degree of conformity to pressure for each of a plurality of connection patterns and determine the connection pattern with the highest degree of conformity. The pipe determination unit 14 may perform this process using a combination optimization algorithm.

The output unit 15 outputs data indicating the metal pipes and the connection order thereof determined by the pipe determination unit 14 to indicate the metal pipes to be deployed and the order of deployment thereof (s15).

In the process shown in FIG. 7, the pipe determination unit 14 may determine the arrangement of metal pipes having pressure resistances suitable for an underground environment based on the underground environment indicated by the use condition data and pressure resistances of these metal pipes indicated by the pipe-specific data. For example, in an oil-well pit in which metal pipes are to be placed, the collapse performance required varies depending on depth and stratigraphic position. The user may input data about the depth of the oil well and stratigraphic position as the use condition data to learn which metal pipes and which order of deployment thereof are suitable for the pressure environment of the oil well.

Embodiment 3

<Process of Determining Arrangement of Metal Pipes with Corrosion Resistances Suitable for Underground Environment>

Figure 8:
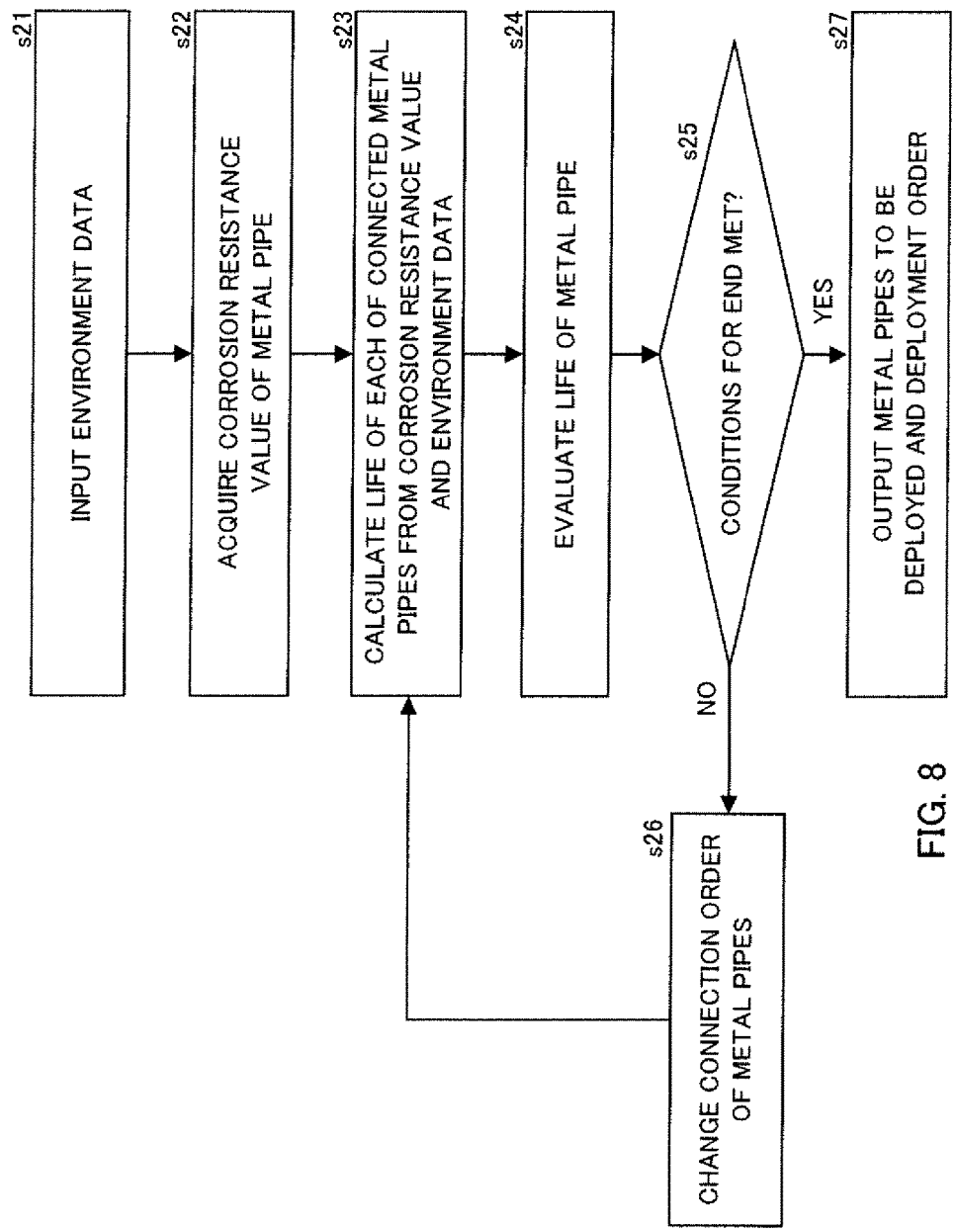
FIG. 8 is a flow chart illustrating a process for deciding on a connection order of metal pipes.

FIG. 8 is a flow chart illustrating an example of a process for deciding on a connection order of metal pipes. In the example shown in FIG. 8, the use condition reception unit 12 acquires, as the use condition data, environment data indicating the environment in which metal pipes are to be placed (s21). The environment data acquired may be data indicating, for example, pressure, temperature, geological features, the amount of a predetermined substance contained in gas or muddy water along the entire length of the oil well in which the metal pipes are to be placed.

The pipe-specific data acquisition unit 13 acquires, as the pipe-specific data, corrosion resistance data indicating the corrosion resistance of each of a plurality of metal pipes (s22). The corrosion resistance data acquired may be, for example, coefficient of corrosion resistance, measured wall thickness or other parameters.

Based on the pressure resistance values of the connected metal pipes and the environment data, the pipe determination unit 14 calculates the life of each of the metal pipes (s23). For example, the life of a metal pipe may be calculated based on the corrosion rate calculated from the coefficient of corrosion resistance of the metal pipe indicated by the pipe-specific data, measured pipe wall thickness and the corrosion environment at the position at which the metal pipe is to be placed (indicated by the environment data). The pipe determination unit 14 evaluates the life calculated at s23 (s24). It is determined based on the result of this evaluation whether the conditions for ending the process are met (s25) and, if not, the connection order of the metal pipes is changed (s26) and the process including s23 to s25 is repeated. Thus, for example, the pipe determination unit 14 may determine the connection order of metal pipes with the longest life of the metal pipes (or a value close to the longest).

The output unit 15 outputs data indicating the metal pipes and the connection order thereof determined by the pipe determination unit 14 to indicate metal pipes to be deployed and the order of deployment thereof (s27).

In the process shown in FIG. 8, the pipe determination unit 14 may determine the arrangement of metal pipes having corrosion resistances suitable for an underground environment based on the underground environment indicated by the use condition data and corrosion resistances of these metal pipes indicated by the pipe-specific data. For example, in an oil-well pit in which metal pipes are to be placed, the corrosion resistance required varies depending on depth and stratigraphic position. The user may input data about the depth of the oil well and stratigraphic position as the use condition data to learn which metal pipes and which order of deployment thereof are suitable for the corrosion environment of the oil well.

Embodiment 4

<Process for Determining Appropriate Connection Relationship Between Metal Pipes>

Figure 9:
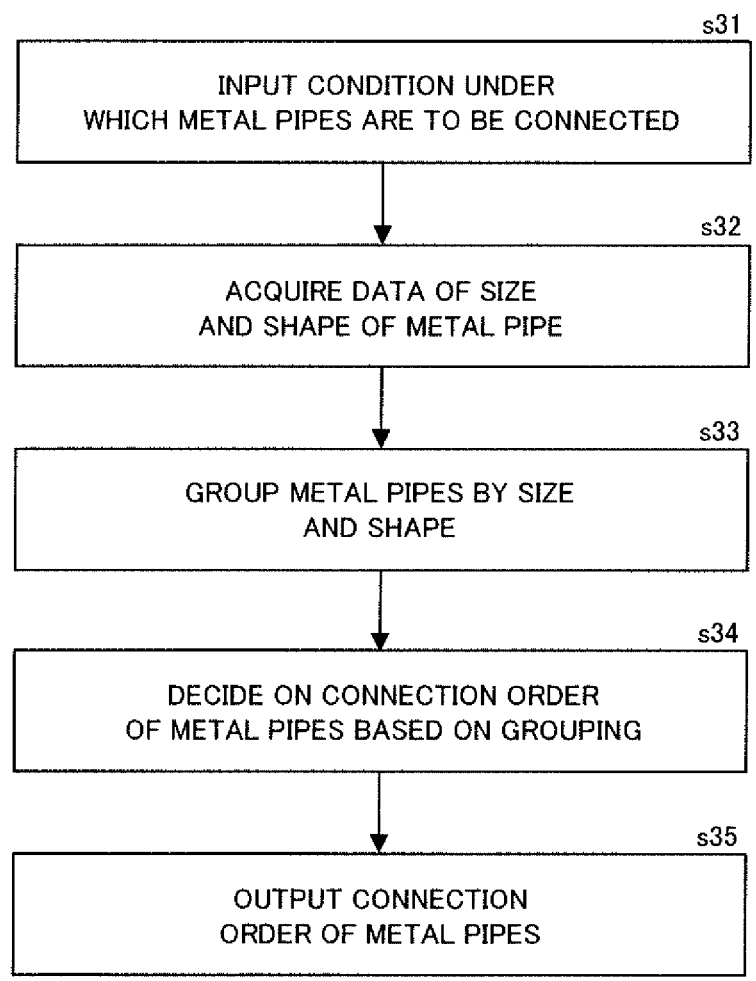
FIG. 9 is a flow chart illustrating a process for deciding on a connection order of metal pipes.

FIG. 9 is a flow chart illustrating an example of a process for deciding on a connection order of metal pipes. In the example shown in FIG. 9, the use condition reception unit 12 acquires a connection condition of metal pipes as the use condition data (s31). The connection condition acquired may be data indicating, for example, the number of metal pipes to be connected.

For example, the pipe-specific data acquisition unit 13 acquires, as the pipe-specific data, measured values of the size and shape of each of a plurality of metal pipes indicated by identification data acquired by the metal pipe information reception unit 11 (s32). For example, the pipe-specific data acquired may be measured pipe outer diameter, measured pipe wall thickness and measured pipe ellipticity.

The pipe determination unit 14 groups metal pipes such that the pipes of each group has similar sizes and shapes (s33) and, based on the grouping, determines the metal pipes to be connected and the connection order of these metal pipes (s34). In the present implementation, it determines the metal pipes to be connected and the connection order of these metal pipes that meet the connection condition input at s31.

For example, the pipe determination unit 14 may select the number of metal pipes indicated by the connection condition and group them at s33. Then, the pipe determination unit 14 may decide on a connection order of the metal pipes in each of the groups determined at s33, and further decide on a connection order of the groups. When the unit decides on a connection order within each group, for example, it may calculate the difference between the outer diameters of the metal pipes to be connected, the difference between the wall thicknesses thereof, and the difference between the ellipticities thereof, and determine the metal pipes and the connection relationship thereof that minimizes these differences as a whole. Similarly, when the unit decides on a connection order of the groups, it may calculate and evaluate the difference between the outer diameters of the metal pipes to be connected from different groups, the difference between the wall thicknesses thereof, and the difference between the ellipticities thereof to decide on a connection order. A combination optimization algorithm, for example, may be used to determine the connection order of metal pipes that ensures that the difference between the outer diameters of metal pipes to be connected, the difference between the wall thicknesses thereof and the difference between the ellipticities thereof are at a minimum or close to a minimum as a whole.

The output unit 15 outputs data indicating the metal pipes and the connection order thereof determined by the pipe determination unit 14 (s35).

In the process shown in FIG. 9, the pipe determination unit 14 may decide on a connection relationship between a plurality of metal pipes to be used based on the sizes and shapes indicated by the pipe-specific data. For example, in metal pipes that need to be welded together, such as line pipes, a small difference in outer diameter, wall thickness, ellipticity or other factors may affect the quality of the welded pipes. The metal-pipe use support system allows the user to learn which joining order is the optimum one when pipes are to be welded together to make a line pipe, for example.

Embodiment 5

<Process for Determining Metal Pipes Appropriate for Processing>

Figure 10:
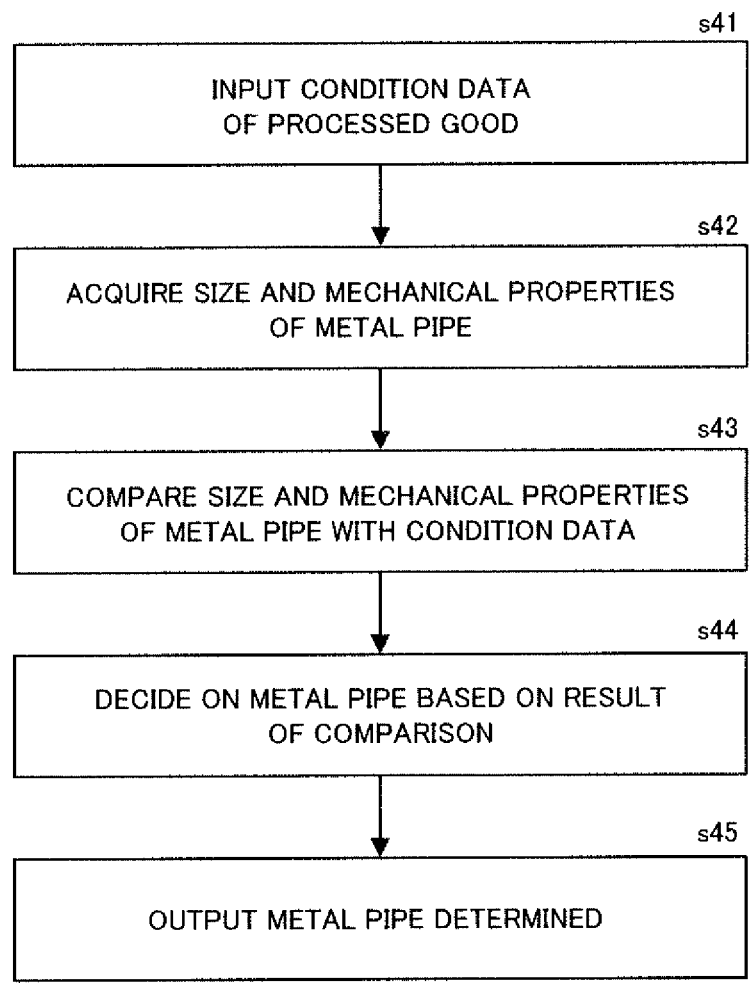
FIG. 10 is a flow chart illustrating a process for determining the metal pipes to be used.

FIG. 10 is a flow chart illustrating an example of a process for deciding on metal pipes to be used. In the example shown in FIG. 10, the use condition reception unit 12 acquires, as the use condition data, condition data indicating conditions required of a processed good made from a metal pipe (s41). The condition data acquired may be data indicating, for example, the size or properties required from the processed good made from the metal pipe. The use condition reception unit 12 may present, to the user, size or property items for which values can be designated as the use condition data. For example, the items of the pipe-specific data stored by the data recording unit 2 may be presented to the user.

For example, the pipe-specific data acquisition unit 13 may acquire, as the pipe-specific data, measured values of the size and mechanical properties of each of a plurality of metal pipes indicated by the identification data acquired by the metal pipe information reception unit 11 (s42). The pipe-specific data reception unit 13 may acquire, for example, the pipe-specific data for items corresponding to the size or properties indicated by the condition data acquired at s41.

The pipe determination unit 14 compares the measured values of the size and mechanical properties of the metal pipes acquired at s42 and the condition data input at s41 (s43) and, based on the result of this comparison, determines the metal pipes to be used from among the plurality of metal pipes (s44). The output unit 15 outputs data indicating the metal pipes and the connection order thereof determined by the pipe determination unit 14 (s45).

In the process shown in FIG. 10, the pipe determination unit 14 may determine, from among a plurality of metal pipes, at least one metal pipe that has properties suitable for the performance required of a processed good indicated by the use condition data. For example, the user may use delivered metal pipes as materials to produce processed goods. The user may input the properties of metal pipes required of the processed goods and, instantly, learn which metal pipes have the size or mechanical properties that are most suitable for the materials of the processed goods.

Embodiment 6

<Process for Determining Metal Pipes not Exceeding Upper Limit of Length>

Figure 11:
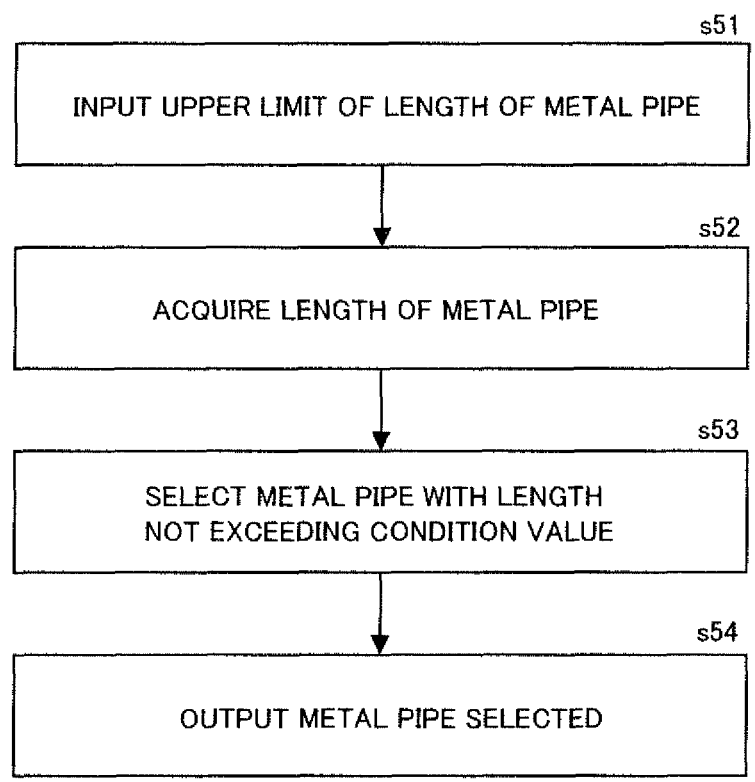
FIG. 11 is a flow chart illustrating a process for determining the metal pipes to be used.

FIG. 11 is a flow chart illustrating an example of a process for determining the metal pipes to be used. In the example shown in FIG. 11, the use condition reception unit 12 acquires an upper limit of the length of metal pipes as the use condition data (s51). The pipe-specific data acquisition unit 13 acquires, as the pipe-specific data, measured pipe lengths of a plurality of metal pipes indicated by identification data acquired by the metal pipe information reception unit 11 (s52). The pipe determination unit 14 selects metal pipes with measured pipe lengths that do not exceed the upper limit acquired at s51 (s53). The output unit 15 outputs data indicating the metal pipes selected at s53 (s54).

In the process shown in FIG. 11, the pipe determination unit 14 may determine, from among a plurality of metal pipes, at least one metal pipe that has a measured length not exceeding the upper limit. For example, the user may store some of the purchased metal pipes in a container to transport them to a destination. In such cases, the user may enter an upper limit of the length of metal pipes that can be stored in the container into the metal-pipe use support system and learn which metal pipes can be transported.

Embodiment 7

<Process for Determining Arrangement of Metal Pipes with Torques Suitable for Risk of Thread Loosening>

Figure 12:
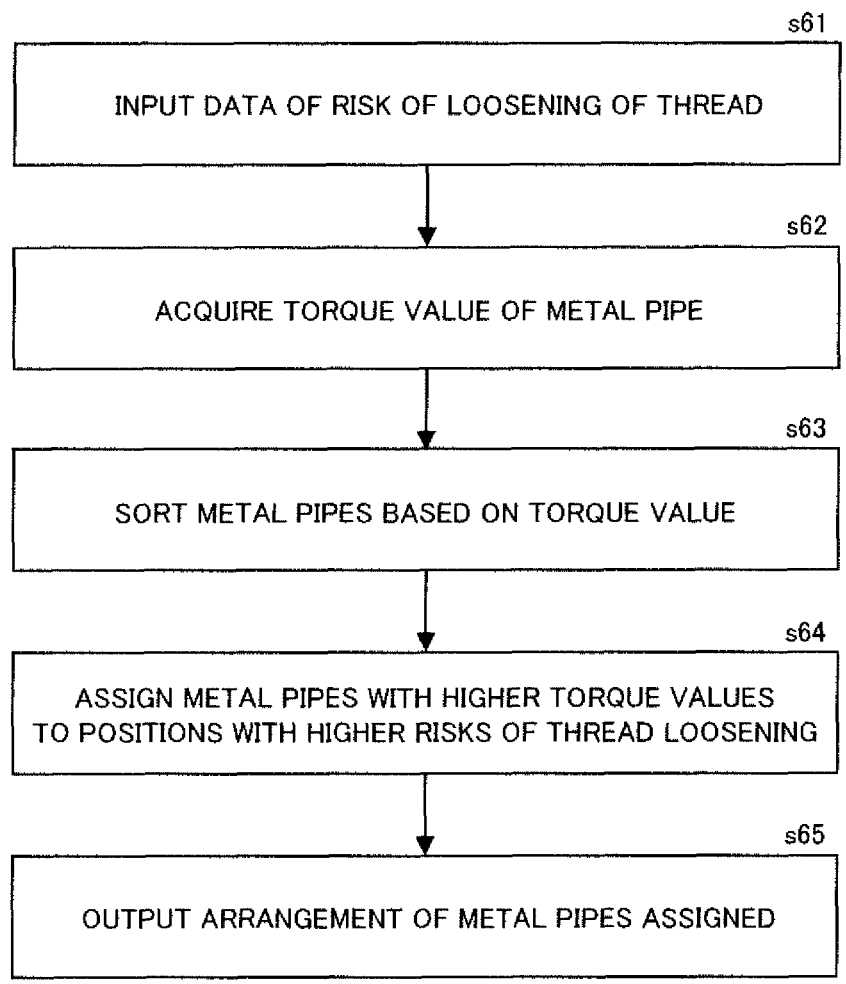
FIG. 12 is a flow chart illustrating a process for deciding on a connection order of metal pipes.

FIG. 12 is a flow chart indicating an example of a process for deciding on a connection order of metal pipes. In the example shown in FIG. 12, the use condition reception unit 12 acquires, as the use condition data, risk data indicative of the degree of risk that a threaded joint for metal pipes tightened during the manufacturing process loosens in an environment in which the metal pipes are placed (s61). The risk data acquired may be data indicating the configuration of the well in which the metal pipes are to be deployed, or the level of risk of refastening in the environment in which the metal pipes are to be placed, for example.

The pipe-specific data acquisition unit 13 acquires, as the pipe-specific data, torque data indicative of tightening torque values for the threaded joints for a plurality of connected metal pipes (s62). For example, the torque data acquired may be tightening torque value.

Based on the torque value, the pipe determination unit 14 rearranges (sorts) the plurality of metal pipes indicated by the identification data acquired by the metal pipe information reception unit 11 (s63). Based on the order of the rearranged metal pipes and the risk data, the pipe determination unit 14 determines the metal pipes to be used and decides on a connection order of these metal pipes (s64).

For example, based on the risk data acquired as the use condition data, the metal determination unit 14 determines the degree of risk at each of the positions in the space in which the metal pipes are to be placed. Then, the pipe determination unit 14 may determine the connection order of the plurality of metal pipes that ensures that a metal pipe having a torque higher than other metal pipes is placed at a position in the space at which the risk is higher than those at other positions. More specifically, the pipe determination unit 14 may divide the space in which the metal pipes are to be placed into a plurality of sections with different risk levels and assign metal pipes sorted at s63 to sections with higher risk levels and then sections with lower risk levels in descending order.

Alternatively, the pipe determination unit 14 may compare the torque values of a plurality of metal pipes connected together and placed and the degrees of risk at these positions and, based on the result of this comparison, perform a process of evaluating the degree of conformity to risk for each of a plurality of connection patterns and determine the connection pattern with the highest degree of conformity. The pipe determination unit 14 may perform this process using a combination optimization algorithm.

The output unit 15 outputs data indicating the metal pipes and the connection order thereof determined by the pipe determination unit 14 to indicate the metal pipes to be deployed and the order of deployment thereof (s65).

In the process shown in FIG. 12, the pipe determination unit 14 may determine the arrangement of metal pipes having tightening torques suitable for the degree of risk of loosening of the thread indicated by the use condition data. For example, a metal pipe for an oil well may be provided with male threads on both ends, on which a female thread on an end of another metal pipe is fastened to form a threaded joint for shipment. Further, in some oil-well structures in which metal pipes are to be deployed, the risk of loosening of a thread may be relatively high at some locations. When the user is to deploy metal pipes in an oil well, for example, he may enter the structure of the oil well into the metal-pipe use support system to obtain information indicating the arrangement of metal pipes with joints tightened at the torque values appropriate for given risks. This enables assigning with preference a metal pipe with a higher torque value than other metal pipes to a location where the risk of loosening of a thread is higher than at other locations. This in turn reduces the risk of loosening of the portions fastened during the manufacturing process.

Embodiment 8

<Process for Determining Arrangement of Metal Pipes Suitable for Risk of Breaking and Corrosion-Induced Wall Thinning>

Figure 13:
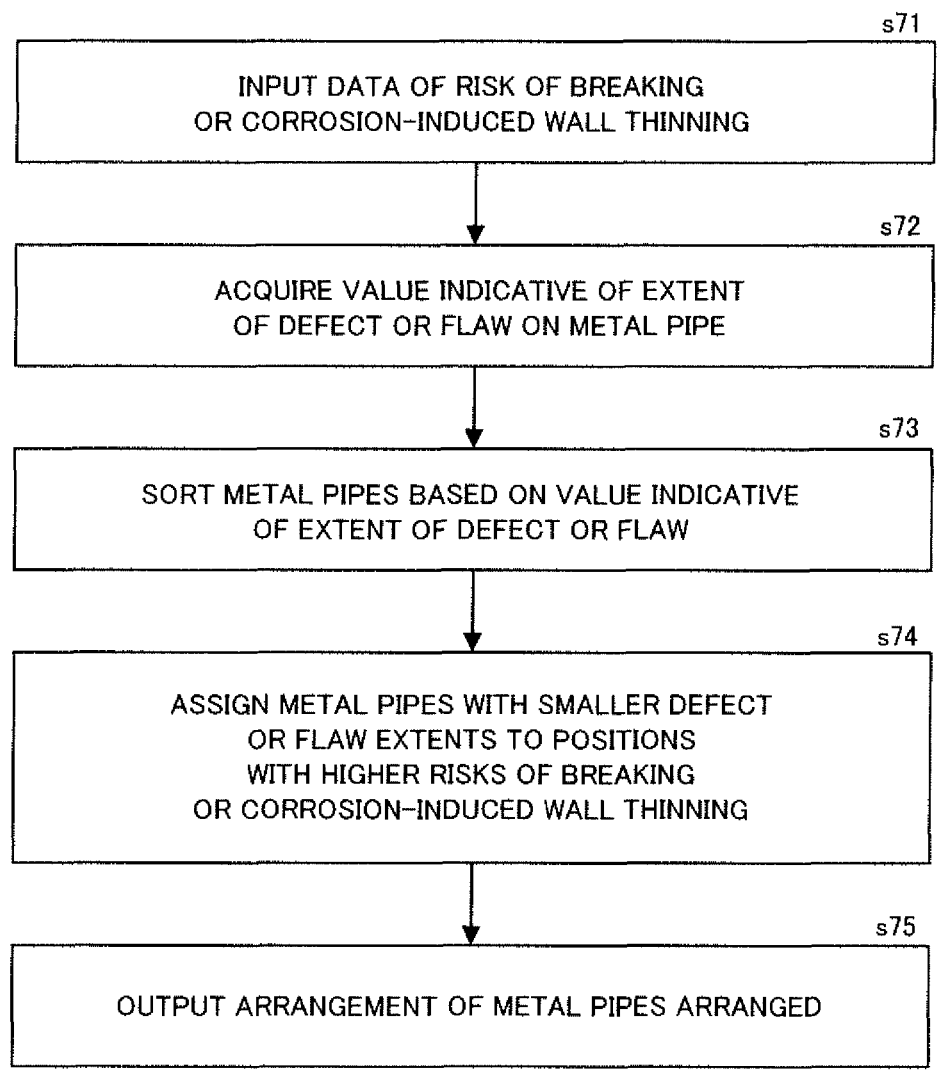
FIG. 13 is a flow chart illustrating a process for deciding on a connection order of metal pipes.

FIG. 13 is a flow chart illustrating an example of a process for deciding on a connection order of metal pipes. In the example shown in FIG. 13, the use condition reception unit 12 acquires, as the use condition data, risk data indicating the degree of risk of breaking of a metal pipe or corrosion-induced wall thinning in an environment in which metal pipes are to be placed (s71). The risk data acquired may be data indicating, for example, the structure of the space in which metal pipes are to be deployed, the distribution of pressure in the space in which metal pipes are to be placed, or the corrosion condition level at each of various positions in the space.

The pipe-specific data acquisition unit 13 acquires, as the pipe-specific data, inspection data indicating the extent of flaws on each of a plurality of metal pipes (s72). The flaws covered by the pipe-specific data may be, for example, discontinuities such as unintended cracks or pits produced during manufacture or use of the metal pipes. Alternatively, the flaws covered may be those unintended discontinuities that were determined to exceed predetermined standards or determined to be defects. The flaws covered are not limited to a particular shape, and may be flaws in various shapes such as flaws that are open on the surface or spaces formed inside. The extent of a flaw may be expressed by a value indicating the extent of a flaw that can be detected, such as the depth, size or shape of a flaw. For example, values obtained from inspections, such as maximum defect depth or maximum flaw depth, may be acquired as inspection data.

The pipe determination unit 14 rearranges (sorts) the plurality of metal pipes indicated by the identification data acquired by the metal pipe information reception unit 11 based on the value indicating the extent of flaws (s73). Based on the order of the rearranged metal pipes and the risk data, the pipe determination unit 14 determines the metal pipes to be used and the connection order of these metal pipes (s74).

For example, based on the risk data acquired as the use condition data, the pipe determination unit 14 determines the degree of risk of breaking or corrosion-induced wall thinning at each of the various positions in the space in which the metal pipes are to be placed. Then, the pipe determination unit 14 may determine the connection order of the metal pipes that ensures that a metal pipe with a smaller flaw extent than other metal pipes is placed at a position in the space at which the risk of breaking or corrosion-induced wall thinning is higher than at other positions. More specifically, the pipe determination unit 14 may divide the space in which the metal pipes are to be placed into a plurality of sections with different levels of risk of breaking or corrosion-induced wall thinning and assign metal pipes sorted at s73 to sections with higher risk levels and then sections with lower risk levels in descending order.

Alternatively, the pipe determination unit 14 may compare the flaw extent of each of the metal pipes connected together and placed and the degree of risk of breaking or corrosion-induced wall thinning at each of these positions and, based on the result of this comparison, perform a process of evaluating the degree of conformity to risk for each of a plurality of connection patterns and determine the connection pattern with the highest degree of conformity. The pipe determination unit 14 may perform this process using a combination optimization algorithm.

The output unit 15 outputs data indicating the metal pipes and connection order thereof determined by the pipe determination unit 14 to indicate the metal pipes to be deployed and the order of deployment thereof (s75).

In the process shown in FIG. 13, the pipe determination unit 14 may determine the arrangement of metal pipes with flaws acceptable under the degree of risk of breaking or corrosion-induced wall thinning indicated by the use condition data. For example, a nondestructive inspection (NDI) of a metal pipe may detect a flaw with a depth within an acceptance range. The above implementation uses data of such a detected flaw to reduce the risk of breaking or corrosion-induced wall thinning when the metal pipe is actually used. For example, when the user is to deploy a metal pipe in an oil well, he may enter oil-well conditions into the metal-pipe use support system to obtain information indicating the arrangement of metal pipes appropriate for a given risk of breaking or corrosion-induced wall thinning. This allows the user to avoid placing a metal pipe with a deep flaw at a position at which the risk of breaking or corrosion-induced wall thinning is higher than at other positions, for example.

Embodiment 9

<Process for Deciding on Combinations of Connected Metal Pipes in Sets>

Figure 14:
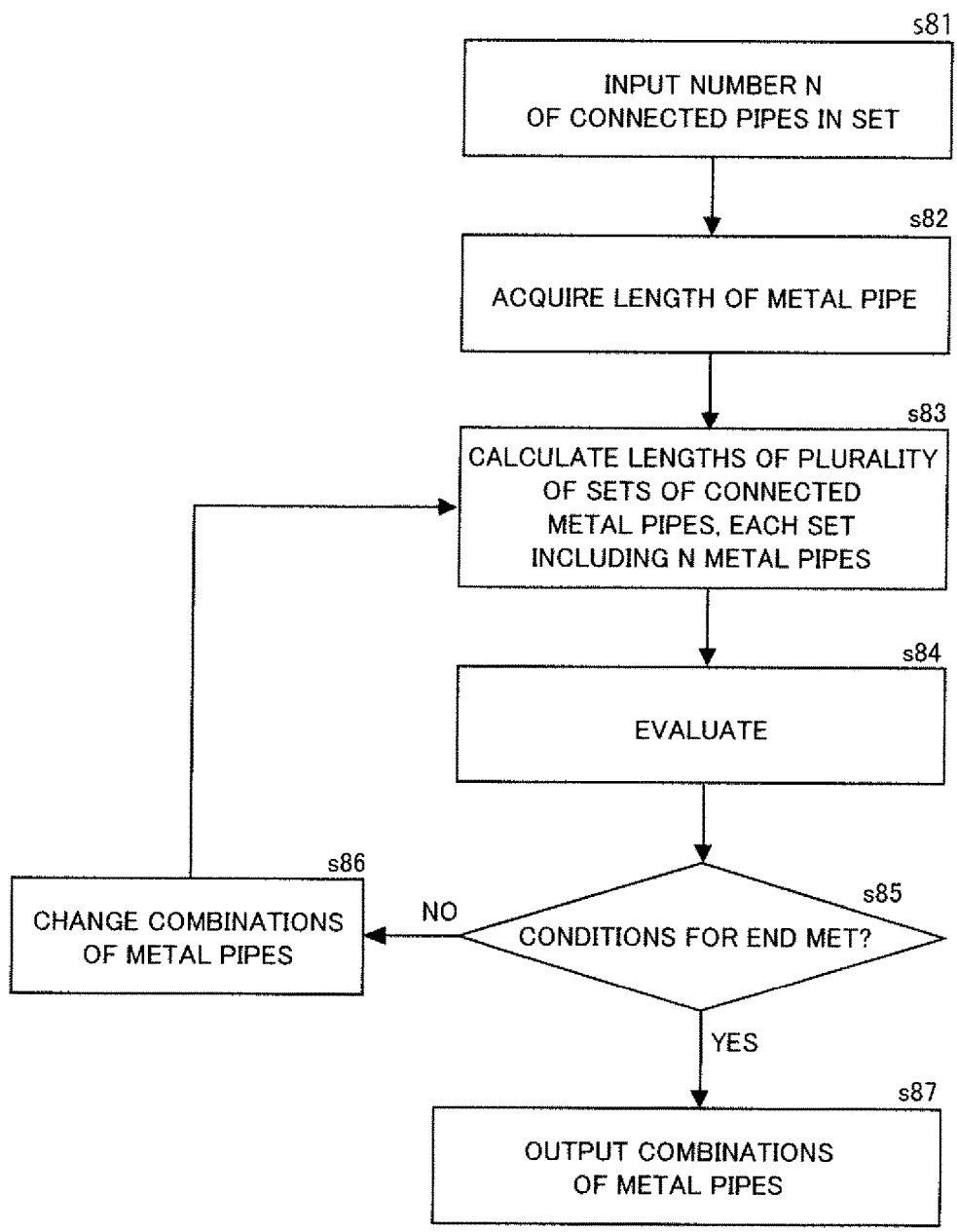
FIG. 14 is a flow chart illustrating a process for deciding on a connection order of metal pipes.

FIG. 14 is a flow chart illustrating an example of a process for deciding on a connection order of metal pipes. In the example shown in FIG. 14, the use condition reception unit 12 acquires, as the use condition data, a number N (N is a natural number greater than 1) of metal pipes connected together to form a set (s81).

The pipe-specific data acquisition unit 13 acquires, as the pipe-specific data, data indicative of the length or weight of each of a plurality of metal pipes (s82). As an example, an implementation where a measured pipe length is acquired as the pipe-specific data will be described.

The pipe determination unit 14 receives the identification data acquired by the metal pipe information reception unit 11 which indicates a plurality of metal pipes, and calculates the entire length of N metal pipes connected together to form a set, where calculation occurs for each of a plurality of sets (s83). The pipe determination unit 14 calculates and evaluates the degree of variation of the lengths of the sets of metal pipes (s84). It is determined based on the result of this calculation whether the conditions for ending the process are met (s85), and if not, the connection order of metal pipes is changed (s86), and the process including s83 to 85 is repeated. Thus, the pipe determination unit 14 may determine the combinations of metal pipes in a plurality of sets that will result in a uniform length of the sets, each set including N connected metal pipes.

The output unit 15 outputs data indicating the combination of metal pipes in each of the sets determined by the pipe determination unit 14 (s87). The above-illustrated implementation acquires the length of metal pipes as the pipe-specific data; alternatively or additionally, the weight of metal pipes may be acquired as the pipe-specific data. In such implementations, the pipe determination unit 14 may determine the combinations of metal pipes in a plurality of sets that will result in a near-uniform weight or a near-uniform length and weight of the sets.

In the process shown in FIG. 14, the pipe determination unit 14 determines the combination of connected metal pipes in each of a plurality of sets that will result in a near-uniform length or weight of the sets of connected metal pipes, each set including a predetermined number of metal pipes. For example, when metal pipes are inserted into an oil-well pit, N (for example, 3) pipes may be connected to form a set in advance before being inserted. The user may enter a number N of pipes in a set into the metal-pipe use support system, for example, to obtain information indicating combinations of metal pipes in sets that will result in a uniform length or weight of the sets of metal pipes as connected, where each set includes N pipes. The uniform length and/or weight of a plurality of sets of connected metal pipes enables improving insertion efficiency and reducing the burden on the insertion equipment.

Embodiment 10

<Process for Determining Appropriate Connection Order of Metal Pipes Depending on a Plurality of Conditions>

Figure 15:
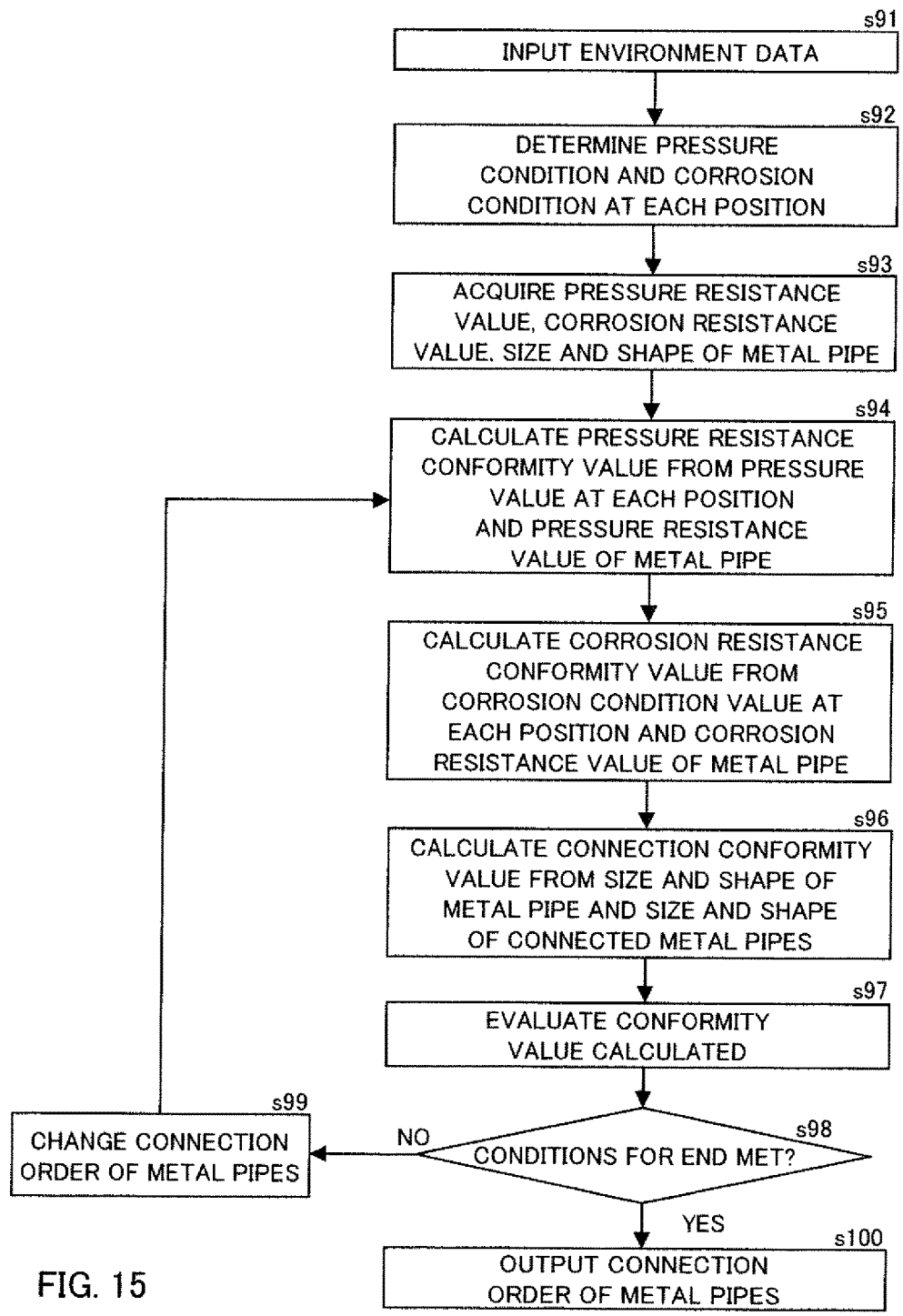
FIG. 15 is a flow chart illustrating a combination of the processes of Embodiments 2, 3 and 4.

At least two of the processes illustrated in Embodiments 2 to 9 may be combined. FIG. 15 is a flow chart illustrating a process with Embodiments 2, 3 and 4 combined together. In the example shown in FIG. 15, the use condition reception unit 12 acquires, as the use condition data, environment data indicative of an environment in which metal pipes are to be placed (s91). The environment data acquired may be data indicating, for example, the depth of the oil well in which metal pipes are to be placed, pressure distribution, the relationship between pressure and depth, geological features, or the amount of a predetermined substance contained in gas or muddy water.

Based on the use condition data acquired, the use condition reception unit 12 determines the pressure condition and corrosion condition at each of various positions at which metal pipes are to be placed (s92). For example, the space in which metal pipes are to be placed is divided into a plurality of sections and the value of pressure or required pressure resistance in each section and the value indicating the corrosion environment are determined. This determination may be performed by the pipe determination unit 14.

The pipe-specific data acquisition unit 13 acquires, as the pipe-specific data, data indicative of the pressure resistance, corrosion resistance, size and shape of each of a plurality of metal pipes (s93). The pipe-specific data acquired may be, for example, collapse strength, coefficient of corrosion resistance, measured pipe wall thickness, measured pipe outer diameter, and measured pipe ellipticity.

The pipe determination unit 14 compares the pressure resistance of each of a plurality of metal pipes connected in a certain order and placed and the pressure condition at the location at which this metal pipe is to be placed to calculate a value about the pressure resistance of each metal pipe (i.e. pressure resistance conformity value) (s94). Further, the pipe determination unit 14 compares the corrosion resistance of each of a plurality of metal pipes connected in a certain order and placed and the corrosion condition at the location at which this metal pipe is to be placed to calculate the degree of conformity of each metal pipe in terms of corrosion resistance (i.e. corrosion resistance conformity value) (s95). Further, the pipe determination unit 14 calculates the difference in size and shape between each metal pipe and another metal pipe to which this metal pipe is connected to calculate the degree of conformity in the connection of these metal pipes (i.e. connection conformity value) (s96).

The pipe determination unit 14 evaluates the pressure resistance conformity value calculated at s94, the corrosion resistance conformity value calculated at s95 and the connection conformity value calculated at s96 (s97). It is determined based on the result of this evaluation whether the conditions for ending the process are met (s98) and, if not, the connection order of metal pipes is changed (s99) and the process including s23 to s25 is repeated. Thus, for example, the pipe determination unit 14 may determine the optimum (or near-optimum) connection order of metal pipes in terms of pressure resistance, corrosion resistance and connection relationship.

The conditions for ending the process at s98 may include, other than the evaluation results discussed above, the number of repetitions of the process of changing the connection order at s99, or the degree of variation of evaluation results. Further, the process of changing the connection order of metal pipes at s99 may include determining whether the connection order is to be changed based on the result of evaluation at s97 or determining whether a change is to be made based on a certain probability.

If it is determined at s97 that the conditions for ending the process are met, the output unit 15 outputs data indicating the connection order of metal pipes determined at s99 by the pipe determination unit 14 (s100).

In the process shown in FIG. 15, the pipe determination unit 14 may determine the connection order of metal pipes that ensures that the metal pipes conform to the environment in which they are used and that metal pipes that conform to each other in size and shape are connected, based on the environment indicated by the use condition data and the pressure resistance, corrosion resistance, size and shape of each of the metal pipes indicated by the pipe-specific data.

Although embodiments of the present invention have been described, the present invention is not limited to the above-illustrated embodiments. The metal pipe of the present invention may be a steel pipe mainly composed of iron and nickel, as well as a metal pipe of any material. Further, the scope of applications of the metal pipe is not limited to oil-well pipe and line pipe applications.

The data stored in the data recording unit 2 is not limited to that illustrated above. For example, data indicating the distribution channel or packing records of metal pipes may be stored so as to be associated with the identification data of the metal pipes. For example, the data recording unit 2 may store data specifying the identification data of a plurality of metal pipes bundled together in packing. In such implementations, the metal pipe information reception unit 11 may identify the identification data of a plurality of metal pipes bundled together by just receiving the identification data of at least one of the metal pipes contained in this bundle that has been read by the user terminal 3. Even though a plurality of metal pipes are bundled together, the user may identify the metal pipes bundled together by reading the identification mark on one metal pipe located on the outside of the bundle.

The invention claimed is:

1. A metal-pipe use support system comprising:
a reading unit configured to read identification data for a plurality of metal pipes,
a metal pipe information reception unit configured to receive, from the reading unit, the identification data for each of the plurality of metal pipes;
a use condition reception unit configured to receive an environment value indicative of an environment at each of positions in a space in which the metal pipes are to be placed as use condition data about a condition under which a metal pipe is to be used;
a pipe-specific data acquisition unit configured to access a data recording unit storing pipe-specific data indicative of a property of each metal pipe and corresponding identification data in an associated manner and to acquire the pipe-specific data associated with the identification data received by the metal pipe information reception unit, the pipe-specific data including a performance value indicative of a performance of each of the metal pipes;
a pipe determination unit configured to assign, by a processor, to each of the positions in the space in which the metal pipes are to be placed, a metal pipe having a performance value suitable for the environment value of that position based on a comparison between the environment value for each of the positions in the space in which the metal pipes are to be placed indicated by the use-condition data and the performance value indicative of the performance of each of the metal pipes included in the pipe-specific data to determine an arrangement of the plurality of metal pipes; and
an output unit configured to output information relating to the metal pipe determined by the pipe determination unit.

2. The metal-pipe use support system according to claim 1, wherein the pipe determination unit decides on a plurality of metal pipes to be used from among the plurality of metal pipes and decides on a connection relationship between a plurality of metal pipes determined to be metal pipes to be used.

3. The metal-pipe use support system according to claim 1, wherein the pipe-specific data acquired by the pipe-specific data acquisition unit includes a measured value of the property of each of the plurality of metal pipes or a value calculated from the measured value.

4. The metal-pipe use support system according to claim 1, wherein the use condition data includes data indicative of an underground environment in which a metal pipe is to be placed, and
the pipe-specific data acquired by the pipe-specific data acquisition unit includes data indicative of a pressure resistance of each of the plurality of metal pipes, wherein, based on the underground environment indicated by the use condition data and the pressure resistance of each of the plurality of metal pipes indicated by the pipe-specific data, the pipe determination unit decides to place a metal pipe that has a pressure resistance suitable for the underground environment to decide on a connection relationship between at least two of the plurality of metal pipes.

5. The metal-pipe use support system according to claim 1, wherein the use condition data includes data indicative of an underground environment in which a metal pipe is to be placed, and the pipe-specific data includes data indicative of a corrosion resistance of each of the plurality of metal pipes, wherein, based on the underground environment indicated by the use condition data and the corrosion resistance of each of the plurality of metal pipes indicated by the pipe-specific data, the pipe determination unit decides to place a metal pipe having a corrosion resistance suitable for the underground environment to decide on a connection relationship between at least two of the plurality of metal pipes.

6. The metal-pipe use support system according to claim 1, wherein the pipe-specific data acquired by the pipe-specific data acquisition unit includes data indicative of a size and shape of each of the plurality of metal pipes, wherein, based on the size and shape indicated by the pipe-specific data, the pipe determination unit decides on a connection relationship between at least two of the plurality of metal pipes.

7. The metal-pipe use support system according to claim 1, wherein the use condition data includes data indicative of a performance required of a processed good made from a metal pipe, wherein the pipe determination unit determines, from among the plurality of metal pipes, at least one metal pipe that has a property meeting the performance required of the processed good indicated by the use condition data.

8. The metal-pipe use support system according to claim 1, wherein the use condition data includes an upper limit of a length of a metal pipe, and the pipe-specific data acquired by the pipe-specific data acquisition unit includes a measured length of each of the plurality of metal pipes, wherein the pipe determination unit determines, from among the plurality of metal pipes, at least one metal pipe having a measured length not exceeding the upper limit.

9. The metal-pipe use support system according to claim 1, wherein the use condition data includes data indicative of a degree of risk that a threaded joint for metal pipes tightened during a manufacture process loosening in an environment in which the metal pipes are placed, and the pipe-specific data acquired by the pipe-specific data acquisition unit includes data indicative of a tightening torque for a threaded joint for the plurality of metal pipes, wherein the pipe determination unit decide to place a metal pipe having a tightening torque suitable for the degree of risk indicated by the use condition data to decide on a connection relationship between at least two of the plurality of metal pipes.

10. The metal-pipe use support system according to claim 1, wherein the use condition data includes data indicative of a degree of risk of breaking or corrosion-induced wall thinning of a metal pipe in an environment in which the metal pipe is to be placed, and the pipe-specific data acquired by the pipe-specific data acquisition unit includes data indicative of a flaw on each of the plurality of metal pipes, wherein the pipe determination unit decides to place a metal pipe having a flaw acceptable under the degree of risk of breaking or corrosion-induced wall thinning indicated by the use condition data to decide on a connection relationship between at least two of the plurality of metal pipes.

11. The metal-pipe use support system according to claim 1, wherein the pipe-specific data includes data indicative a length and weight of each of the plurality of metal pipes, wherein, when a predetermined number of metal pipes are connected to form a set and a plurality of such sets are provided, the pipe determination unit determines a combination of the predetermined number of metal pipes in each set that will result in a near-uniform length or weight of the sets of metal pipes.

12. A method of using metal pipes, comprising:

controlling, by a computer, a reading unit to read identification data for a plurality of metal pipes;

receiving, by the computer, from the reading unit, the identification data for each of the plurality of metal pipes;

receiving, by the computer, an environment value indicative of an environment at each of positions in a space in which the metal pipes are to be placed as use condition data about a condition under which a metal pipe is to be used;

accessing, by the computer, a data recording unit storing pipe-specific data indicative of a property of each metal pipe and corresponding identification data in an associated manner to acquire the pipe-specific data associated with the received identification data, the pipe-specific data including a performance value indicative of a performance of each of the metal pipes;

assigning, by the computer, to each of the positions in the space in which the metal pipes are to be placed, a metal pipe having a performance value suitable for the environment value of that position based on a comparison between the environment value for each of the positions in the space in which the metal pipes are to be placed indicated by the use-condition data and the performance value indicative of the performance of each of the metal pipes included in the pipe-specific data to determine an arrangement of the plurality of metal pipes; and outputting, by the computer, information relating to the determined arrangement of the plurality of metal pipes; and placing the plurality of metal pipes in accordance with the output information relating to the arrangement of the plurality of metal pipes.

13. A non-transitory computer-readable medium storing a program causing a computer to execute a process comprising:

controlling a reading unit to read identification marks on a plurality of metal pipes;

receiving, from the reading unit, identification data for each of the plurality of metal pipes;

receiving an environment value indicative of an environment at each of positions in a space in which the metal pipes are to be placed as use condition data about a condition under which a metal pipe is to be used;

accessing a data recording unit storing pipe-specific data indicative of a property of each metal pipe and corresponding identification data in an associated manner to acquire the pipe-specific data associated with the received identification data, the pipe-specific data including a performance value indicative of a performance of each of the metal pipes;

assigning, to each of the positions in the space in which the metal pipes are to be placed, a metal pipe having a performance value suitable for the environment value of that position based on a comparison between the environment value for each of the positions in the space in which the metal pipes are to be placed indicated by the use-condition data and the performance value indicative of the performance of each of the metal pipes included in the pipe-specific data to determine an arrangement of the plurality of metal pipes; and outputting information relating to the determined metal pipe.

\* \* \* \* \*